(12) United States Patent
Liang et al.

(10) Patent No.: US 8,270,689 B2
(45) Date of Patent: *Sep. 18, 2012

(54) APPARATUS FOR CARIES DETECTION

(75) Inventors: Rongguang Liang, Penfield, NY (US);
Victor C. Wong, Rochester, NY (US);
Michael A. Marcus, Honeoye Falls, NY (US); Mark E. Bridges, Spencerport, NY (US); Paul O. McLaughlin, Rochester, NY (US); Peter D. Burns, Fairport, NY (US); David L. Patton, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 1742 days.

This patent is subject to a terminal disclaimer.

(21) Appl. No.: 11/530,987

(22) Filed: Sep. 12, 2006

(65) Prior Publication Data

US 2008/0063998 A1    Mar. 13, 2008

(51) Int. Cl.
*G06K 9/00* (2006.01)
(52) U.S. Cl. .......... 382/128; 382/132; 382/254; 433/29; 433/30
(58) Field of Classification Search .................. 382/128, 382/132, 254; 433/29, 30, 215; 348/66; 356/497; 702/71; 600/246, 247; 601/136, 601/145
See application file for complete search history.

(56) References Cited

U.S. PATENT DOCUMENTS

| | | |
|---|---|---|
| 3,971,954 A | 7/1976 | Kleinberg et al. |
| 4,290,433 A | 9/1981 | Alfano |
| 4,479,499 A | 10/1984 | Alfano |
| 4,515,476 A | 5/1985 | Ingmar |
| 5,321,501 A | 6/1994 | Swanson et al. |
| 5,570,182 A | 10/1996 | Nathel et al. |
| 5,742,700 A | 4/1998 | Yoon et al. |
| 5,882,315 A | 3/1999 | Ji et al. |
| 6,122,103 A | 9/2000 | Perkins et al. |

(Continued)

FOREIGN PATENT DOCUMENTS

GB    2 341 943 A    3/2000

(Continued)

OTHER PUBLICATIONS

Fried et al.; "Imaging caries lesions and lesion progression with polarization sensitive optical coherence tomography" Journal of Biomedical Optics, vol. 7, No. 4, Oct. 2002, pp. 618-627.

(Continued)

*Primary Examiner* — Ali Bayat

(57) ABSTRACT

An apparatus for obtaining an image of a tooth having at least one light source providing incident light having a first spectral range for obtaining a reflectance image (122) from the tooth and a second spectral range for exciting a fluorescence image (120) from the tooth. A polarizing beamsplitter (18) in the path of the incident light from both sources directs light having a first polarization state toward the tooth and directs light from the tooth having a second polarization state along a return path toward a sensor (68), wherein the second polarization state is orthogonal to the first polarization state. A first lens (22) in the return path directs image-bearing light from the tooth toward the sensor (68), and obtains image data from the portion of the light having the second polarization state. A long-pass filter (15) in the return path attenuates light in the second spectral range.

29 Claims, 30 Drawing Sheets

U.S. PATENT DOCUMENTS

| | | | |
|---|---|---|---|
| 6,179,611 | B1 | 1/2001 | Everett et al. |
| 6,231,338 | B1 | 5/2001 | de Josselin de Jong et al. |
| 6,449,041 | B1 | 9/2002 | Jung et al. |
| 6,485,300 | B1 * | 11/2002 | Muller et al. .................... 433/29 |
| 6,522,407 | B2 * | 2/2003 | Everett et al. ................ 356/369 |
| 7,102,634 | B2 | 9/2006 | Kim et al. |
| 7,577,284 | B2 | 8/2009 | Wong et al. |
| 7,596,253 | B2 | 9/2009 | Wong et al. |
| 2001/0052979 | A1 | 12/2001 | Treado et al. |
| 2002/0051642 | A1 | 5/2002 | Hicks |
| 2002/0154269 | A1 | 10/2002 | Liu et al. |
| 2004/0202356 | A1 | 10/2004 | Stookey et al. |
| 2004/0240716 | A1 | 12/2004 | de Josselin de Jong et al. |
| 2005/0003323 | A1 * | 1/2005 | Katsuda et al. ................. 433/29 |
| 2005/0024646 | A1 | 2/2005 | Quadling et al. |
| 2005/0182321 | A1 | 8/2005 | Frangioni |
| 2005/0231717 | A1 | 10/2005 | Hsu et al. |

FOREIGN PATENT DOCUMENTS

| | | |
|---|---|---|
| JP | 2004-344260 | 12/2004 |
| WO | WO 03/068064 | 8/2003 |
| WO | WO 2004/032731 | 4/2004 |
| WO | WO 2007/053293 | 5/2007 |
| WO | WO 2007/127036 | 11/2007 |

OTHER PUBLICATIONS

E. R. Dougherty; An Introduction to Morphological Image Processing; SPIE Optical Engineering Press, 1992, Ch. 1.

W. K. Pratt; Digital Image Processing; John Wiley and Sons, New York, 1978, pp. 562-566.

G. A. Baxes; Digital Image Processing Principles and Applications; John Wiley, New York, 1994, pp. 91-95.

Thomas Stehle, "Removal of Specular Reflections in Endoscopic Images," ACTA Polytechnica: Journal of Advanced Engineering, vol. 46, No. 4, 2006, pp. 32-36, XP002476869.

International Search Report, International Application No. PCT/US2007/018982, Feb. 5, 2008.

* cited by examiner

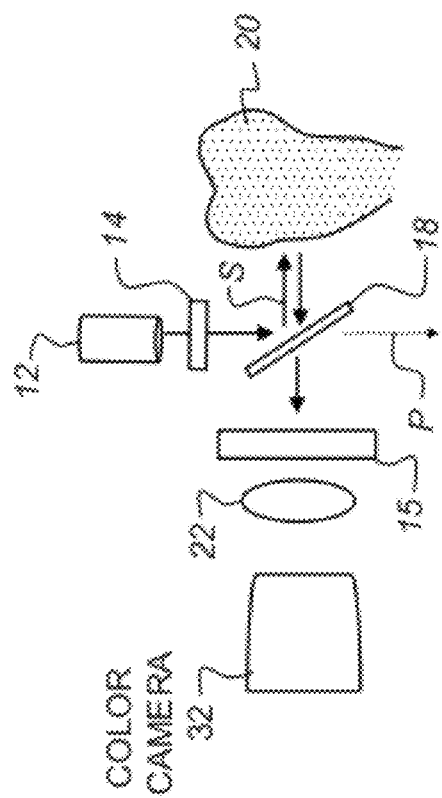
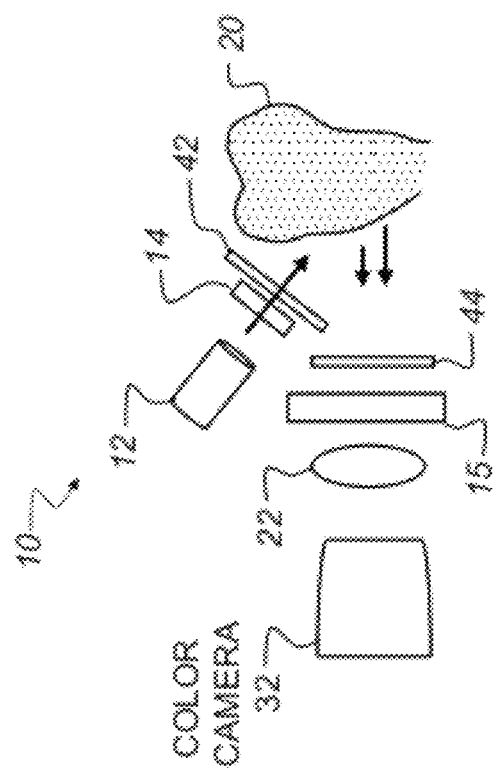
FIG. 4B
FIG. 4A

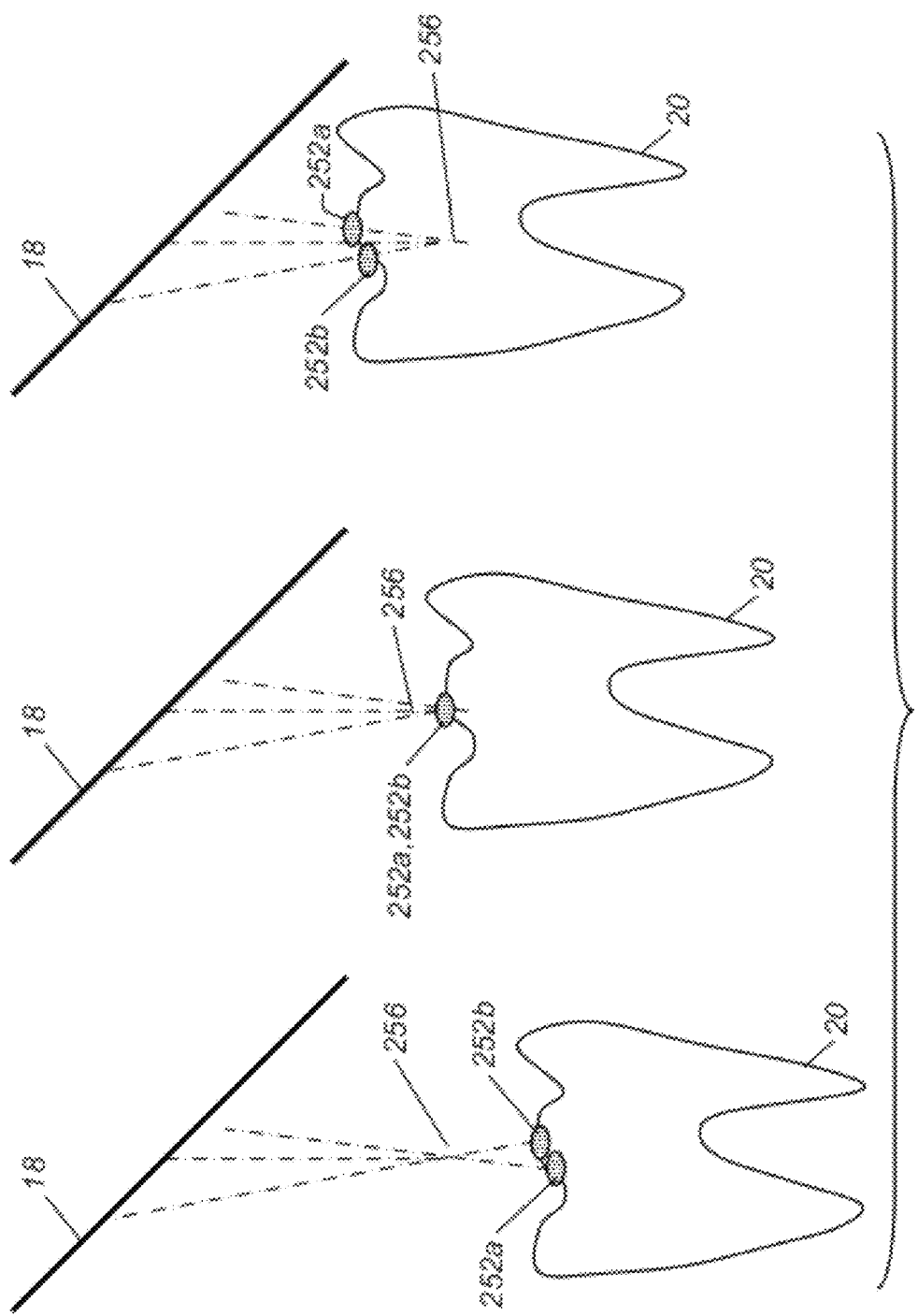

APPARATUS FOR CARIES DETECTION

CROSS REFERENCE TO RELATED APPLICATIONS

Reference is made to commonly-assigned copending U.S. application Ser. No. 11/262,869, filed Oct. 31, 2005, entitled METHOD FOR DETECTION OF CARIES, by Wong et al.; U.S. application Ser. No. 11/408,360, filed Apr. 21, 2006, entitled OPTICAL DETECTION OF DENTAL CARIES by Wong et al.; and U.S. patent application Ser. No. 11/530,913, filed Sep. 12, 2006, entitled LOW COHERENCE DENTAL OCT IMAGING, by Liang et al., the disclosures of which are incorporated herein.

FIELD OF THE INVENTION

This invention generally relates to methods and apparatus for dental imaging and more particularly relates to an apparatus for caries detection using fluorescence and scattering.

BACKGROUND OF THE INVENTION

In spite of improvements in detection, treatment, and prevention techniques, dental caries remains a widely prevalent condition affecting people of all age groups. If not properly and promptly treated, caries can lead to permanent tooth damage and even to loss of teeth.

Traditional methods for caries detection include visual examination and tactile probing with a sharp dental explorer device, often assisted by radiographic (x-ray) imaging. Detection using these methods can be somewhat subjective, varying in accuracy due to many factors, including practitioner expertise, location of the infected site, extent of infection, viewing conditions, accuracy of x-ray equipment and processing, and other factors. There are also hazards associated with conventional detection techniques, including the risk of damaging weakened teeth and spreading infection with tactile methods as well as exposure to x-ray radiation. By the time caries is evident under visual and tactile examination, the disease is generally in an advanced stage, requiring a filling and, if not timely treated, possibly leading to tooth loss.

In response to the need for improved caries detection methods, there has been considerable interest in improved imaging techniques that do not employ x-rays. One method that has been commercialized employs fluorescence, caused when teeth are illuminated with high intensity blue light. This technique, termed quantitative light-induced fluorescence (QLF), operates on the principle that sound, healthy tooth enamel yields a higher intensity of fluorescence under excitation from some wavelengths than does de-mineralized enamel that has been damaged by caries infection. The strong correlation between mineral loss and loss of fluorescence for blue light excitation is then used to identify and assess carious areas of the tooth. A different relationship has been found for red light excitation, a region of the spectrum for which bacteria and bacterial by-products in carious regions absorb and fluoresce more pronouncedly than do healthy areas.

Among proposed solutions for optical detection of caries are the following:

U.S. Pat. No. 4,290,433 (Alfano) discloses a method to detect caries by comparing the excited luminescence in two wavelengths.

U.S. Pat. No. 4,479,499 (Alfano) describes a method to detect caries by comparing the intensity of the light scattered at two different wavelengths.

U.S. Pat. No. 4,515,476 (Ingmar) discloses use of a laser for providing excitation energy that generates fluorescence at some other wavelength for locating carious areas.

U.S. Pat. No. 6,231,338 (de Josselin de Jong et al.) discloses an imaging apparatus for identifying dental caries using fluorescence detection.

U.S. Patent Application No. 2004/0240716 (de Josselin de Jong et al.) discloses methods for improved image analysis for images obtained from fluorescing tissue.

Among commercialized products for dental imaging using fluorescence behavior is the QLF Clinical System from Inspektor Research Systems BV, Amsterdam, The Netherlands. Using a different approach, the Diagnodent Laser Caries Detection Aid from KaVo Dental GmbH, Biberach, Germany, detects caries activity monitoring the intensity of fluorescence of bacterial by-products under illumination from red light.

U.S. Patent Application Publication 2005/0003323 (Katsuda et al.) describes a hand-held imaging apparatus suitable for medical or dental applications, using fluorescence imaging. The '3323 Katsuda et al. disclosure shows an apparatus that receives the reflection light from the diagnostic object and/or the fluorescence of the diagnostic object with different light irradiation. The disclosed apparatus is fairly complicated, requiring switchable filters in the probe, for example. While the apparatus disclosed in the Katsuda et al. '3323 patent application takes advantage of combining reflection light and fluorescence from the diagnostic object in the same optical path, the apparatus does not remove or minimize specular reflection. Any unwanted specular reflection produces false positive results in reflectance imaging. Moreover, with the various illumination embodiments disclosed, the illumination directed toward a tooth or other diagnostic object is not uniform, since the light source is in close proximity to the diagnostic object.

U.S. Patent Application Publication 2004/0202356 (Stookey et al.) describes mathematical processing of spectral changes in fluorescence in order to detect caries in different stages with improved accuracy. Acknowledging the difficulty of early detection when using spectral fluorescence measurements, the '2356 Stookey et al. disclosure describes approaches for enhancing the spectral values obtained, effecting a transformation of the spectral data that is adapted to the spectral response of the camera that obtains the fluorescent image.

While the disclosed methods and apparatus show promise in providing non-invasive, non-ionizing imaging methods for caries detection, there is still room for improvement. One recognized drawback with existing techniques that employ fluorescence imaging relates to image contrast. The image provided by fluorescence generation techniques such as QLF can be difficult to assess due to relatively poor contrast between healthy and infected areas. As noted in the '2356 Stookey et al. disclosure, spectral and intensity changes for incipient caries can be very slight, making it difficult to differentiate non-diseased tooth surface irregularities from incipient caries.

Overall, it is well-recognized that, with fluorescence techniques, the image contrast that is obtained corresponds to the severity of the condition. Accurate identification of caries using these techniques often requires that the condition be at a more advanced stage, beyond incipient or early caries, because the difference in fluorescence between carious and sound tooth structure is very small for caries at an early stage. In such cases, detection accuracy using fluorescence techniques may not show marked improvement over conventional methods. Because of this shortcoming, the use of fluorescence effects appears to have some practical limits that prevent accurate diagnosis of incipient caries. As a result, a caries condition may continue undetected until it is more serious, requiring a filling, for example.

Detection of caries at very early stages is of particular interest for preventive dentistry. As noted earlier, conventional techniques generally fail to detect caries at a stage at which the condition can be reversed. As a general rule of thumb, incipient caries is a lesion that has not penetrated substantially into the tooth enamel. Where such a caries lesion is identified before it threatens the dentin portion of the tooth, remineralization can often be accomplished, reversing the early damage and preventing the need for a filling. More advanced caries, however, grows increasingly more difficult to treat, most often requiring some type of filling or other type of intervention.

In order to take advantage of opportunities for non-invasive dental techniques to forestall caries, it is necessary that caries be detected at the onset. In many cases, as is acknowledged in the '2356 Stookey et al. disclosure, this level of detection has been found to be difficult to achieve using existing fluorescence imaging techniques, such as QLF. As a result, early caries can continue undetected, so that by the time positive detection is obtained, the opportunity for reversal using low-cost preventive measures can be lost.

U.S. Pat. No. 6,522,407 (Everett et al.) discloses the application of polarimetry principles to dental imaging. One system described in the Everett et al. '407 teaching provides a first polarizer in the illumination path for directing a polarized light to the tooth. A second polarizer is provided in the path of reflected light. In one position, the polarizer transmits light of a horizontal polarization. Then, the polarizer is oriented to transmit light having an orthogonal polarization. Intensity of these two polarization states of the reflected light can then be compared to calculate the degree of depolarization of light scattered from the tooth. The result of this comparison then provides information on a detected caries infection.

While the approach disclosed in the Everett et al. '407 patent takes advantage of polarization differences that can result from backscattering of light, the apparatus and methods described therein require the use of multiple polarizers, one in the illumination path, the other in the imaging path. Moreover, the imaging path polarizer must somehow be readily switchable between a reference polarization state and its orthogonal polarization state. Thus, this solution has inherent disadvantages for allowing a reduced package size for caries detection optics. It would be advantageous to provide a simpler solution for caries imaging, a solution not concerned with measuring a degree of depolarization, thus using a smaller number of components and not requiring switchable orientation of a polarizer between one of two positions.

As is described in one embodiment of the Everett et al. '407 patent disclosure, optical coherence tomography (OCT) has been proposed as a tool for dental and periodontal imaging, as well as for other medical imaging applications. For example:
U.S. Pat. No. 5,321,501 (Swanson et al.) describes principles of OCT scanning and measurement as used in medical imaging applications;
U.S. Pat. No. 5,570,182 (Nathel et al.) describes the use of OCT for imaging of tooth and gum structures;
U.S. Pat. No. 6,179,611 (Everett et al.) describes a dental explorer tool that is configured to provide a scanned OCT image;
U.S. Patent Application Publication No. 2005/0024646 (Quadling et al.) describes the use of time-domain and Fourier-domain OCT systems for dental imaging;
Japanese Patent Application Publication No. JP 2004-344260 (Kunitoshi et al.) discloses an optical diagnostic apparatus equipped with a camera for visual observation of a tooth part, with visible light for illuminating a surface image, and an OCT device for scanning the indicated region of a surface image using an alternate light source.

While OCT solutions, such as those described above, can provide very detailed imaging of structure beneath the surface of a tooth, OCT imaging itself can be time-consuming and computation-intensive. OCT images would be most valuable if obtained within one or more local regions of interest, rather than obtained over widespread areas. That is, once a dental professional identifies a specific area of interest, then OCT imaging could be provided for that particular area only. Conventional solutions, however, have not combined visible light imaging with OCT imaging in the same imaging apparatus.

Thus, it can be seen that there is a need for a non-invasive, non-ionizing imaging method for caries detection that offers improved accuracy for detection of caries, particularly in its earlier stages, with a reduced number of components and reduced complexity over conventional solutions.

SUMMARY OF THE INVENTION

The present invention provides an apparatus for imaging a tooth comprising:
(a) at least one light source providing incident light having a first spectral range for obtaining a reflectance image on the tooth and a second spectral range for exciting a fluorescence image of the tooth;
(b) a polarizing beamsplitter in a path of the incident light, the polarizing beamsplitter directing light having a first polarization state toward the tooth and directing light from the tooth having a second polarization state along a return path toward a sensor, wherein the second polarization state is orthogonal to the first polarization state;
(c) a lens positioned in the return path to direct image-bearing light from the tooth toward the sensor for obtaining image data from the portion of the light having the second polarization state; and
(d) a long-pass filter in the return path, to attenuate light in the second spectral range and to transmit light in the first spectral range.

It is a feature of the present invention that it utilizes both fluorescence and reflectance image data for dental imaging.

It is an advantage of the present invention that it offers enhancement over existing fluorescence imaging techniques, useful for detection of caries in its incipient stages.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

FIG. 4A is a schematic block diagram of an imaging apparatus for caries detection according to an alternate embodiment using polarized light;

FIG. 4B is a schematic block diagram of an imaging apparatus for caries detection according to an alternate embodiment using a polarizing beamsplitter to provide polarized light;

FIG. 23C is a diagram showing how focusing indicators operate;

DETAILED DESCRIPTION OF THE INVENTION

Figure 1:
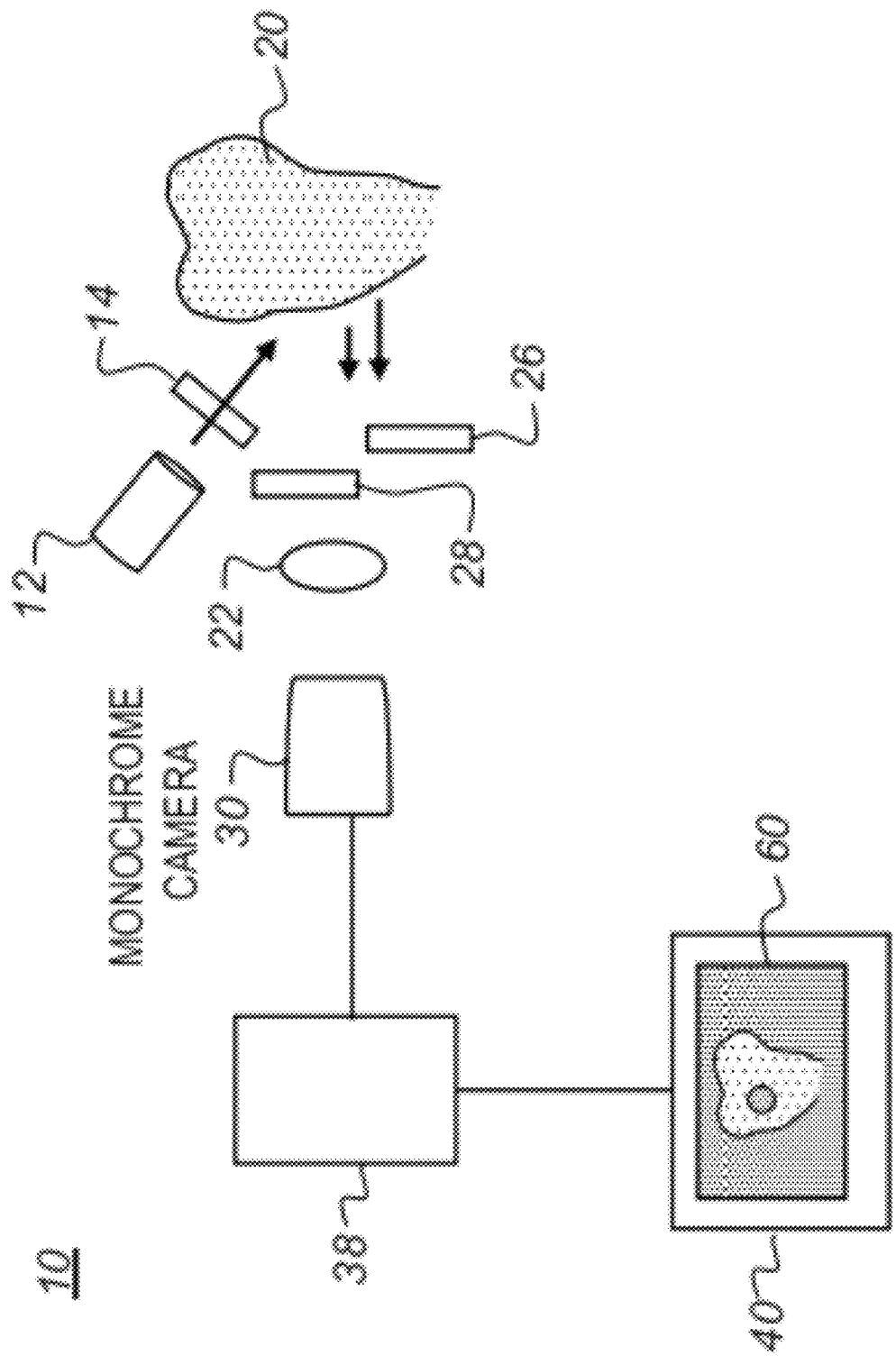
FIG. 1 is a schematic block diagram of an imaging apparatus for caries detection according to one embodiment.

The present description is directed in particular to elements forming part of, or cooperating more directly with, apparatus in accordance with the invention. It is to be understood that elements not specifically shown or described may take various forms well known to those skilled in the art.

As noted in the preceding background section, it is known that fluorescence can be used to detect dental caries using either of two characteristic responses: First, excitation by a blue light source causes healthy tooth tissue to fluoresce in the green spectrum. Secondly, excitation by a red light source can cause bacterial by-products, such as those indicating caries, to fluoresce in the red spectrum.

In order for an understanding of how light is used in the present invention, it is important to give more precise definition to the terms "reflectance" and "back-scattering" as they are used in biomedical applications in general and, more particularly, in the method and apparatus of the present invention. In broadest optical parlance, reflectance generally denotes the sum total of both specular reflectance and scattered reflectance. (Specular reflection is that component of the excitation light that is reflected by the tooth surface at the same angle as the incident angle.) In biomedical applications, however, as in the dental application of the present invention, the specular component of reflectance is of no interest and is, instead, generally detrimental to obtaining an image or measurement from a sample. The component of reflectance that is of interest for the present application is from back-scattered light only. Specular reflectance must be blocked or otherwise removed from the imaging path. With this distinction in mind, the term "back-scattered reflectance" is used in the present application to denote the component of reflectance that is of interest. "Back-scattered reflectance" is defined as that component of the excitation light that is elastically back-scattered over a wide range of angles by the illuminated tooth structure. "Reflectance image" data, as this term is used in the present invention, refers to image data obtained from back-scattered reflectance only, since specular reflectance is blocked or kept to a minimum. In the scientific literature, back-scattered reflectance may also be referred to as back-reflectance or simply as backscattering. Back-scattered reflectance is at the same wavelength as the excitation light.

It has been shown that light scattering properties differ between sound and carious dental regions. In particular, reflectance of light from the illuminated area can be at measurably different levels for normal versus carious areas. This change in reflectance, taken alone, may not be sufficiently pronounced to be of diagnostic value when considered by itself, since this effect is very slight, although detectable. For more advanced stages of caries, for example, back-scattered reflectance may be less effective an indicator than at earlier stages.

In conventional fluorescence measurements such as those obtained using QLF techniques, reflectance itself is an effect that is avoided rather than utilized. A filter is usually employed to block off all excitation light from reaching the detection device. For this reason, the slight but perceptible change in back-scattered reflectance from excitation light has received little attention for diagnosing caries.

The inventors have found, however, that this back-scattered reflectance change can be used in conjunction with fluorescence effects to more clearly and more accurately pinpoint a carious location. Moreover, the inventors have observed that the change in light scattering activity, while it can generally be detected wherever a caries condition exists, is more pronounced in areas of incipient caries. This back-scattered reflectance change is evident at early stages of caries, even when fluorescent effects are least pronounced.

The present invention takes advantage of the observed back-scattering behavior for incipient caries and uses this effect, in combination with fluorescence effects described previously in the background section, to provide an improved capability for dental imaging to detect caries. The inventive technique, hereafter referred to as fluorescence imaging with reflectance enhancement (FIRE), not only helps to increase the contrast of images over that of earlier approaches, but also makes it possible to detect incipient caries at stages where preventive measures are likely to effect remineralization, repairing damage done by the caries infection at a stage well before more complex restorative measures are necessary. Advantageously, FIRE detection can be accurate at an earlier stage of caries infection than has been exhibited using existing fluorescence approaches that measure fluorescence alone.

Imaging Apparatus

Referring to FIG. 1, there is shown one basic optical arrangement for an imaging apparatus 10 for caries detection using the FIRE method in one embodiment. A light source 12 directs an incident light, at a blue wavelength range or other suitable wavelength range, toward tooth 20 through an optional lens 14 or other light beam conditioning component. The tooth 20 may be illuminated at a smooth surface (as shown) or at an occlusal surface (not shown). Two components of light are then detected by a monochrome camera 30 through a lens 22: a back-scattered light component having the same wavelength as the incident light and having measurable reflectance; and a fluorescent light that has been excited due to the incident light. For FIRE imaging, specular reflection causes false positives and is undesirable. To minimize specular reflection pick up, the camera 30 is positioned at a suitable angle with respect to the light source 12. This allows imaging of back-scattered light without the confounding influence of a specularly reflected component.

In the embodiment of FIG. 1, monochrome camera 30 has color filters 26 and 28. One of color filters 26 or 28 is used during reflectance imaging; the other is used during fluorescence imaging. A processing apparatus 38 obtains and processes the reflectance and fluorescence image data and forms a FIRE image 60. FIRE image 60 is an enhanced diagnostic image that can be printed or can appear on a display 40. FIRE image 60 data can also be transmitted to storage or transmitted to another site for display.

Figure 2:
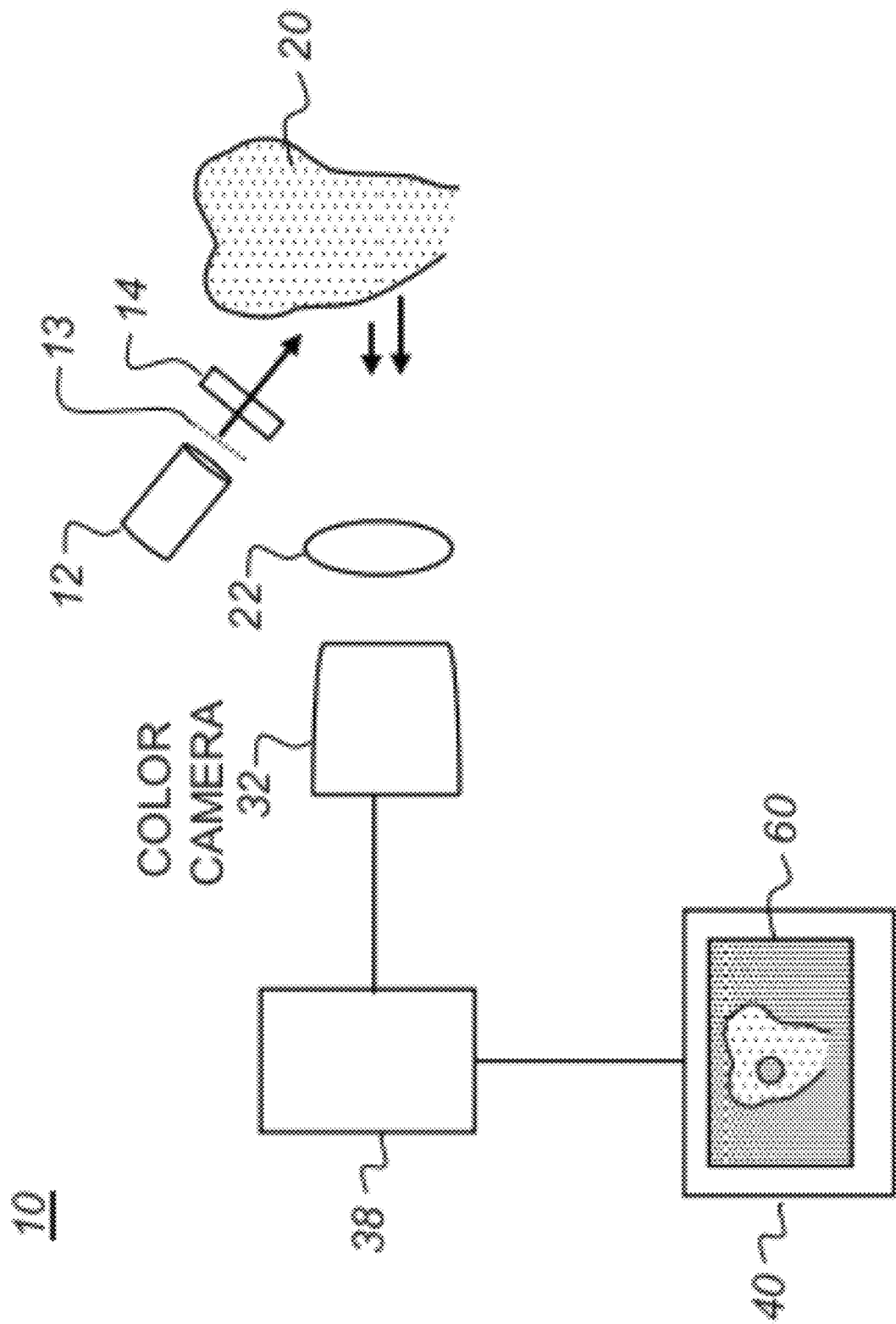
FIG. 2 is a schematic block diagram of an imaging apparatus for caries detection according to an alternate embodiment.

Referring to FIG. 2, there is shown the basic optics arrangement in an alternate embodiment using a color camera 32. With this arrangement, auxiliary filters would not generally be needed, since color camera 32 would be able to obtain the reflectance and fluorescence images from the color separations of the full color image of tooth 20.

Light source 12 is typically centered around a blue wavelength, such as about 405 nm in one embodiment. In practice, light source 12 could emit light ranging in wavelength from an upper ultraviolet range to blue, between about 300 and 500 nm. Light source 12 can be a laser or could be fabricated using one or more light emitting diodes (LEDs). Alternately, a broadband source, such as a xenon lamp, having a supporting color filter for passing the desired wavelengths could be used. Lens 14 or other optical elements may serve to condition the incident light, such as by controlling the uniformity and size of the illumination area. For example, a diffuser 13, shown as a dotted line in FIG. 2, might be used before or after lens 14 to smooth out the hot spots of an LED beam. The path of illumination light might include light guiding or light distributing structures such as an optical fiber or a liquid light guide, for example (not shown). Light level is typically a few milliwatts in intensity, but can be more or less, depending on the light conditioning and sensing components used.

Figure 3:
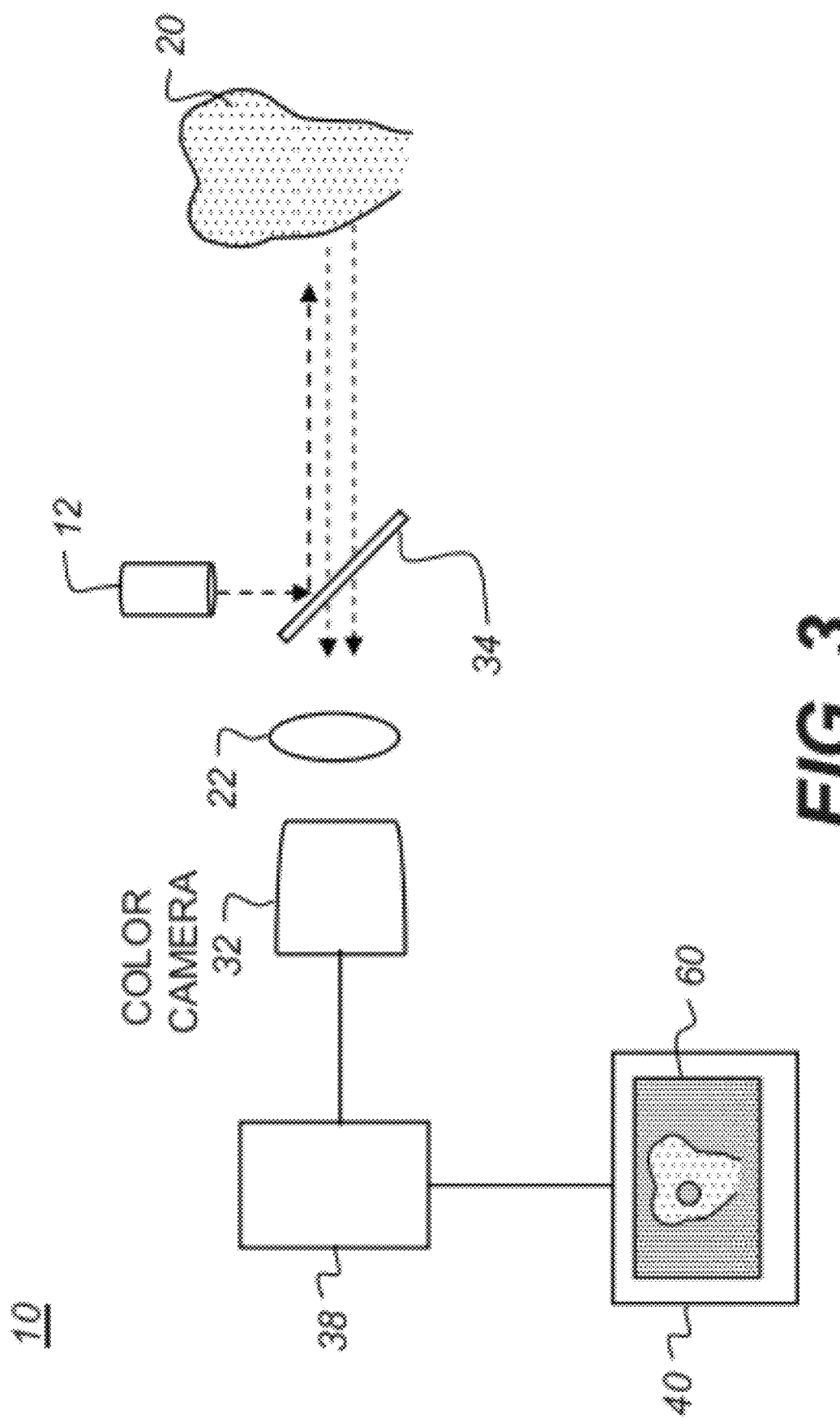
FIG. 3 is a schematic block diagram of an imaging apparatus for caries detection according to an alternate embodiment.
Figure 12A:
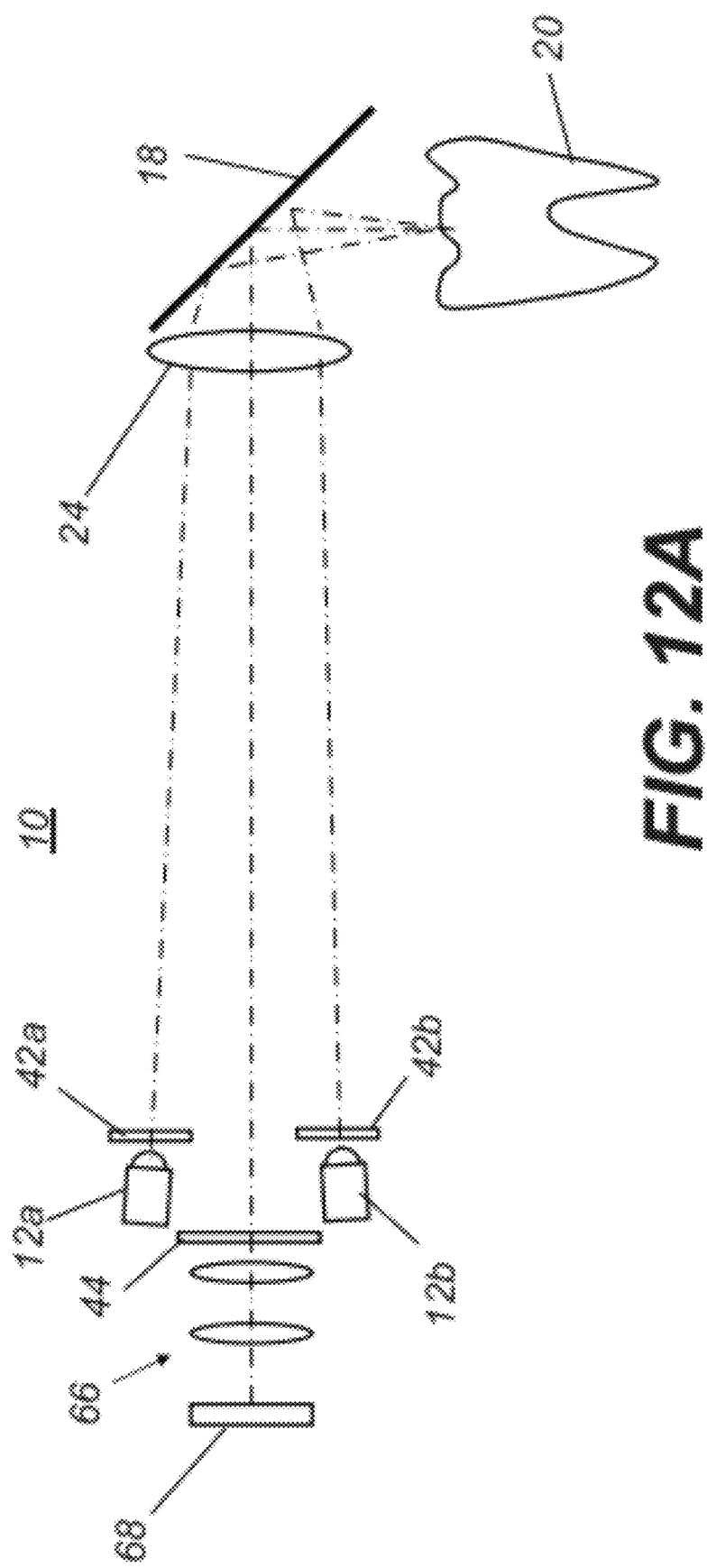
FIG. 12A is a schematic block diagram of an imaging apparatus for caries detection using polarized light from two sources in an alternate embodiment of the present invention.
Figure 12B:
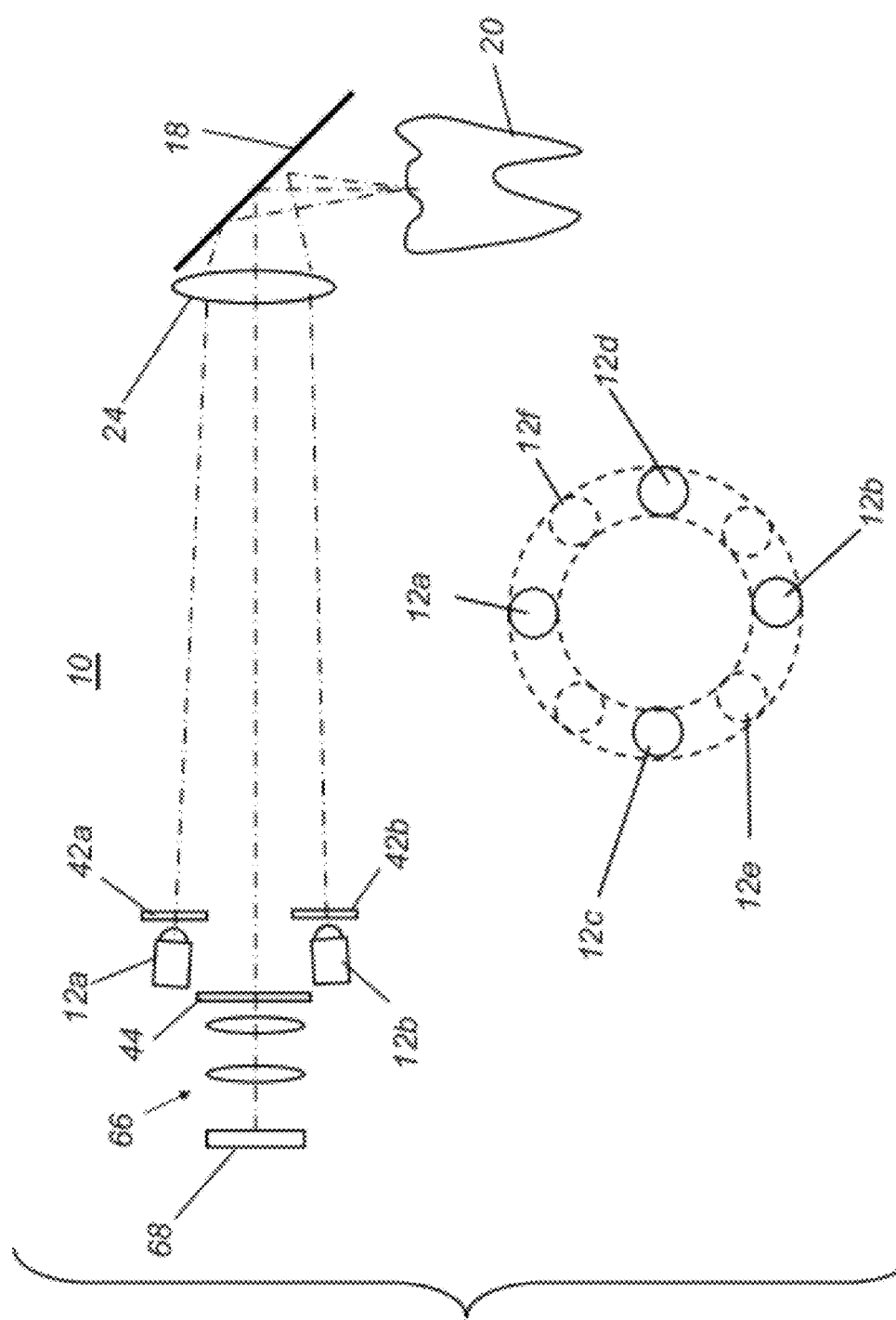
FIG. 12B is a schematic block diagram of an imaging apparatus for caries detection using a ring illuminator with LEDs in an alternate embodiment of the present invention.
Figure 12C:
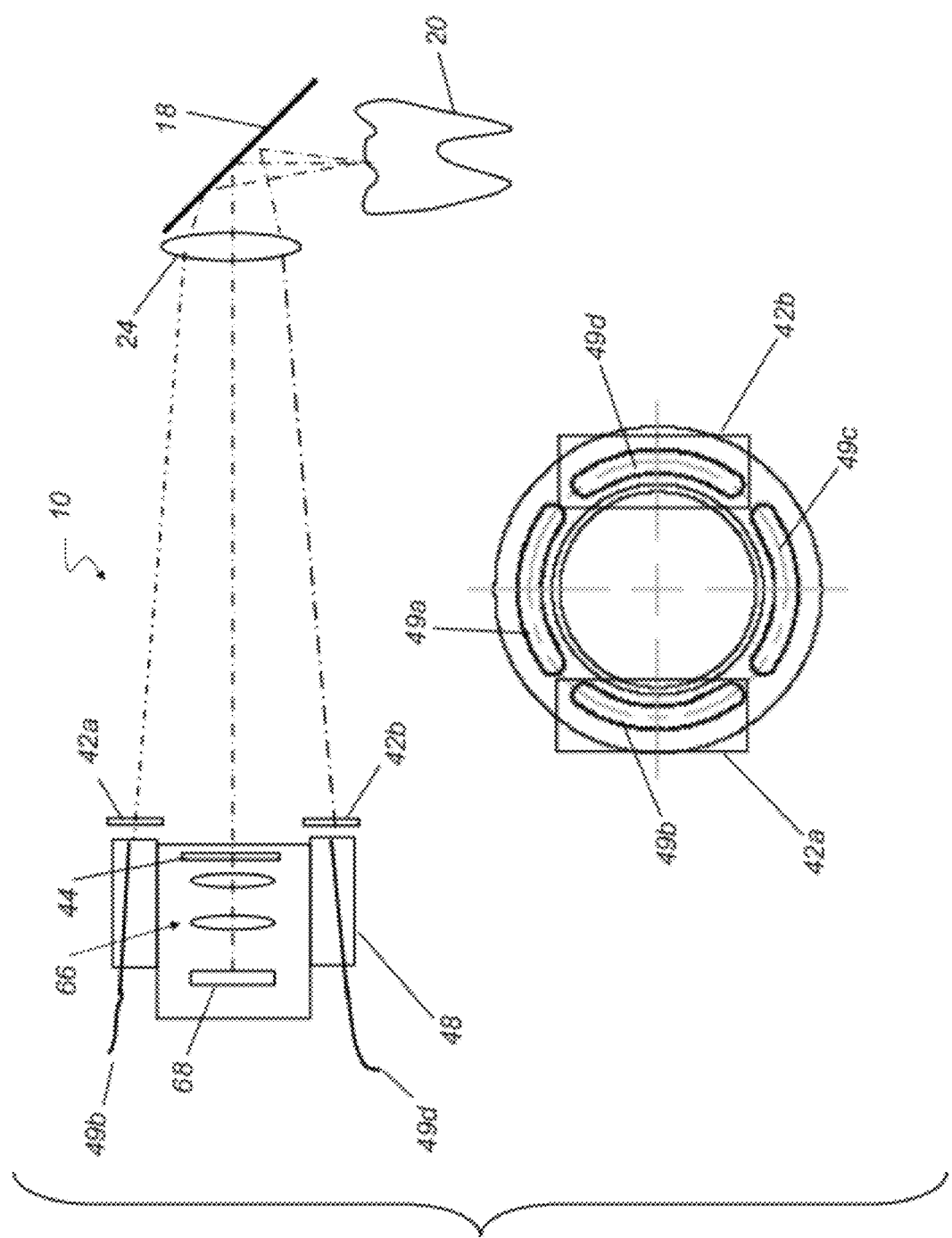
FIG. 12C is a schematic block diagram of an imaging apparatus for caries detection using a fiber ring illuminator in an alternate embodiment of the present invention.

Referring to the basic optical arrangement shown in FIG. 3, illumination components could alternately direct light at normal incidence, turned through a beamsplitter 34. Camera 32 would then be disposed to obtain the image light that is transmitted through beamsplitter 34. Other options for illumination include multiple light sources directed at the tooth with angular incidence from one or more sides. Alternately, the illumination might use an annular ring or an arrangement of LED sources distributed about a center such as in a circular array to provide light uniformly from multiple angles as shown in FIGS. 12A and 12B. Illumination could also be provided through an optical fiber or fiber array as shown in FIG. 12C.

The imaging optics, represented as lens 22 in FIGS. 1-3, could include any suitable arrangement of optical components, with possible configurations ranging from a single lens component to a multi-element lens. Clear imaging of the tooth surface, which is not flat but can have areas that are both smoothly contoured and highly ridged, requires that imaging optics have sufficient depth of field. Preferably, for optimal resolution, the imaging optics provides an image size that substantially fills the sensor element of the camera.

Image capture can be performed by either monochrome camera 30 (FIG. 1) or color camera 32 (FIG. 2). Typically, camera 30 or 32 employs a CMOS or CCD sensor. The monochrome version would typically employ a retractable spectral filter 26, 28 suitable for the wavelength of interest. For light source 12 having a blue wavelength, spectral filter 26 for capturing reflectance image data would transmit predominately blue light. Spectral filter 28 for capturing fluorescence image data would transmit light at a different wavelength, such as predominately green light. Preferably, spectral filters 26 and 28 are automatically switched into place to allow capture of both reflectance and fluorescence images in very close succession. Both images are obtained from the same position to allow accurate registration of the image data.

Spectral filter 28 would be optimized with a pass-band that captures fluorescence data over a range of suitable wavelengths. The fluorescent effect that has been obtained from tooth 20 can have a relative broad spectral distribution in the visible range, with light emitted that is outside the wavelength range of the light used for excitation. The fluorescent emission is typically between about 450 nm and 600 nm, while generally peaking in the green region, roughly from around 510 nm to about 550 nm. Thus a green light filter is generally preferred for spectral filter 28 in order to obtain this fluorescence image at its highest energy levels. With color camera 32, the green image data is generally used for this same reason. This green image data is also obtained through a green light filter, such as a green filter in a color filter array (CFA), as is well known to those skilled in the color image capture art. However, other ranges of the visible spectrum could also be used in other embodiments.

Camera controls are suitably adjusted for obtaining each type of image. For example, when capturing the fluorescence image, it is necessary to make appropriate exposure adjustments for gain, shutter speed, and aperture, since this image may not be intense. When using color camera 32 (FIG. 2), color filtering is performed by the color filter arrays on the camera image sensor. The reflectance image is captured in the blue color plane; simultaneously, the fluorescence image is captured in the green color plane. That is, a single exposure captures both back-scattered reflectance and fluorescence images.

Processing apparatus 38 is typically a computer workstation but may, in its broadest application, be any type of control logic processing component or system that is capable of obtaining image data from camera 30 or 32 and executing image processing algorithms upon that data to generate the FIRE image 60 data. Processing apparatus 38 may be local or may connect to image sensing components over a networked interface.

Figure 5:
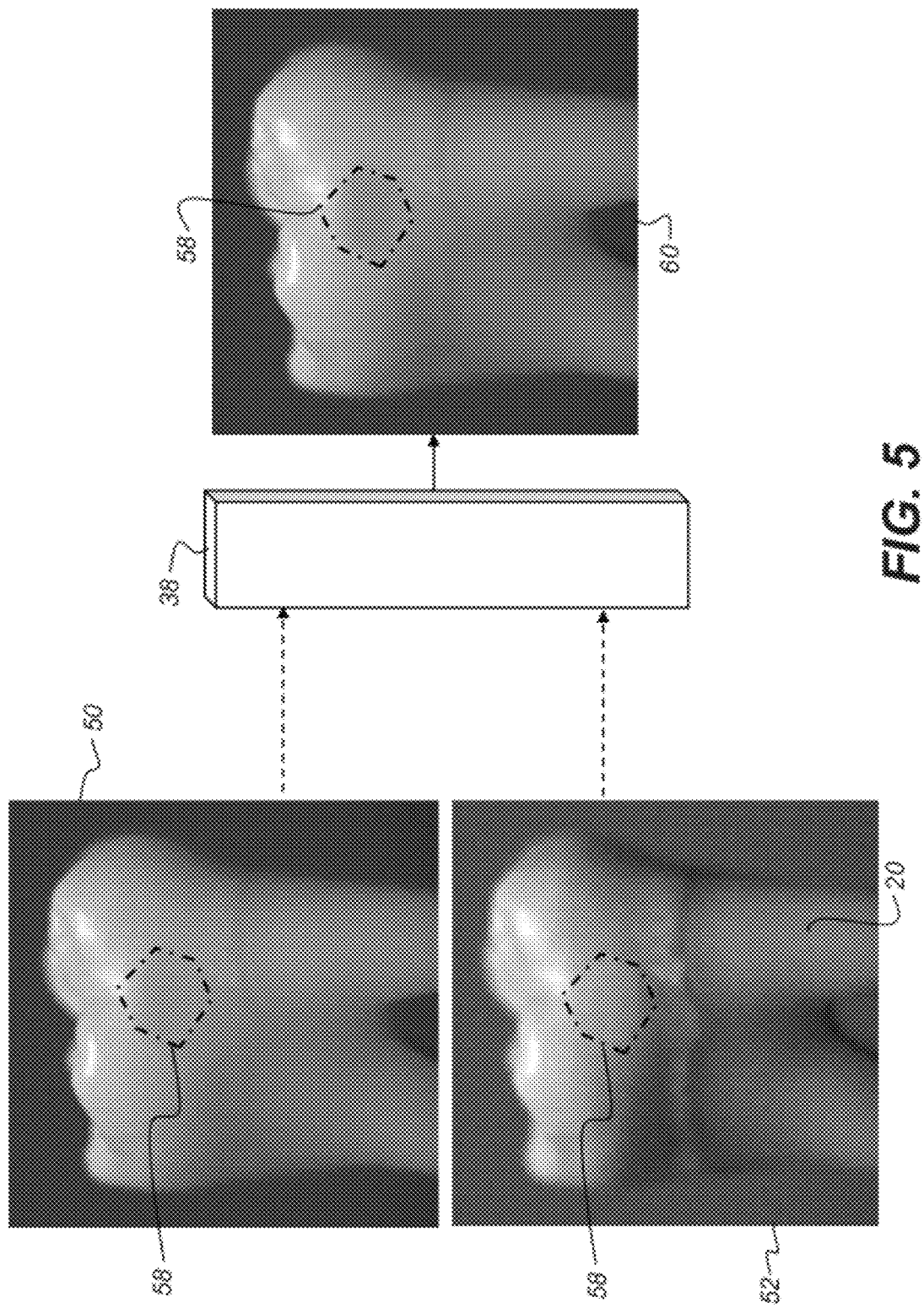
FIG. 5 is a view showing the process for combining dental image data to generate a fluorescence image with reflectance enhancement according to the present invention.

Referring to FIG. 5, there is shown, in schematic form, how the FIRE image 60 is formed according to the present invention. Two images of tooth 20 are obtained, a green fluorescence image 50 and a blue reflectance image 52. As noted earlier, it must be emphasized that the reflectance light used for reflectance image 52 and its data is from back-scattered reflectance, with specular reflectance blocked or kept as low as possible. In the example of FIG. 5, there is a carious region 58, represented in phantom outline in each of images 50, 52, and 60, which causes a slight decrease in fluorescence and a slight increase in reflectance. The carious region 58 may be imperceptible or barely perceptible in either fluorescence image 50 or reflectance image 52, taken individually. Processing apparatus 38 operates upon the image data using an image processing algorithm as discussed below for both images 50 and 52 and provides FIRE image 60 as a result. The contrast between carious region 58 and sound tooth structure is heightened, so that a caries condition is made more visible in FIRE image 60.

Figure 6:
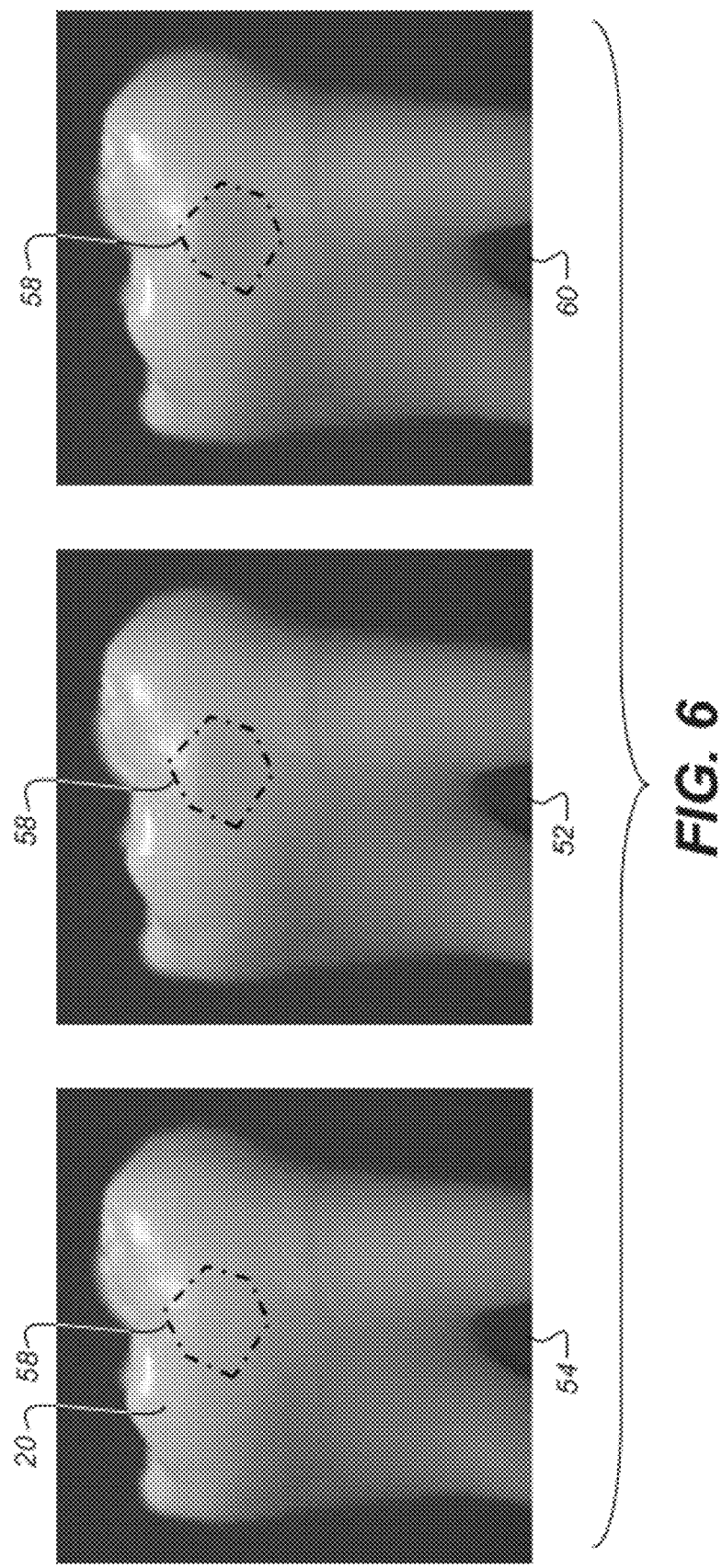
FIG. 6 is a composite view showing the contrast improvement of the present invention in a side-by-side comparison with conventional visual and fluorescence methods.

FIG. 6 shows the contrast improvement of the present invention in a side-by-side comparison with a visual white-light image 54 and conventional fluorescence methods. For caries at a very early stage, the carious region 58 may look indistinct from the surrounding healthy tooth structure in white-light image 54, either as perceived directly by eye or as captured by an intraoral camera. In the green fluorescence image 52 captured by existing fluorescence method, the carious region 58 may show up as a very faint, hardly noticeable shadow. In contrast, in the FIRE image 60 generated by the present invention, the same carious region 58 shows up as a darker, more detectable spot. Clearly, the FIRE image 60, with its contrast enhancement, offers greater diagnostic value.

Image Processing

As described earlier with reference to FIGS. 5 and 6, processing of the image data uses both the reflectance and fluorescence image data to generate a final image that can be used to identify carious areas of the tooth. There are a number of alternative processing methods for combining the reflectance and fluorescence image data to form FIRE image 60 for diagnosis. Commonly-assigned U.S. patent application Ser. No. 11/262,869, cited above, describes one method for combining reflectance and fluorescence image data, using scalar multipliers and finding a difference between scaled reflectance and fluorescence values.

Figure 7:
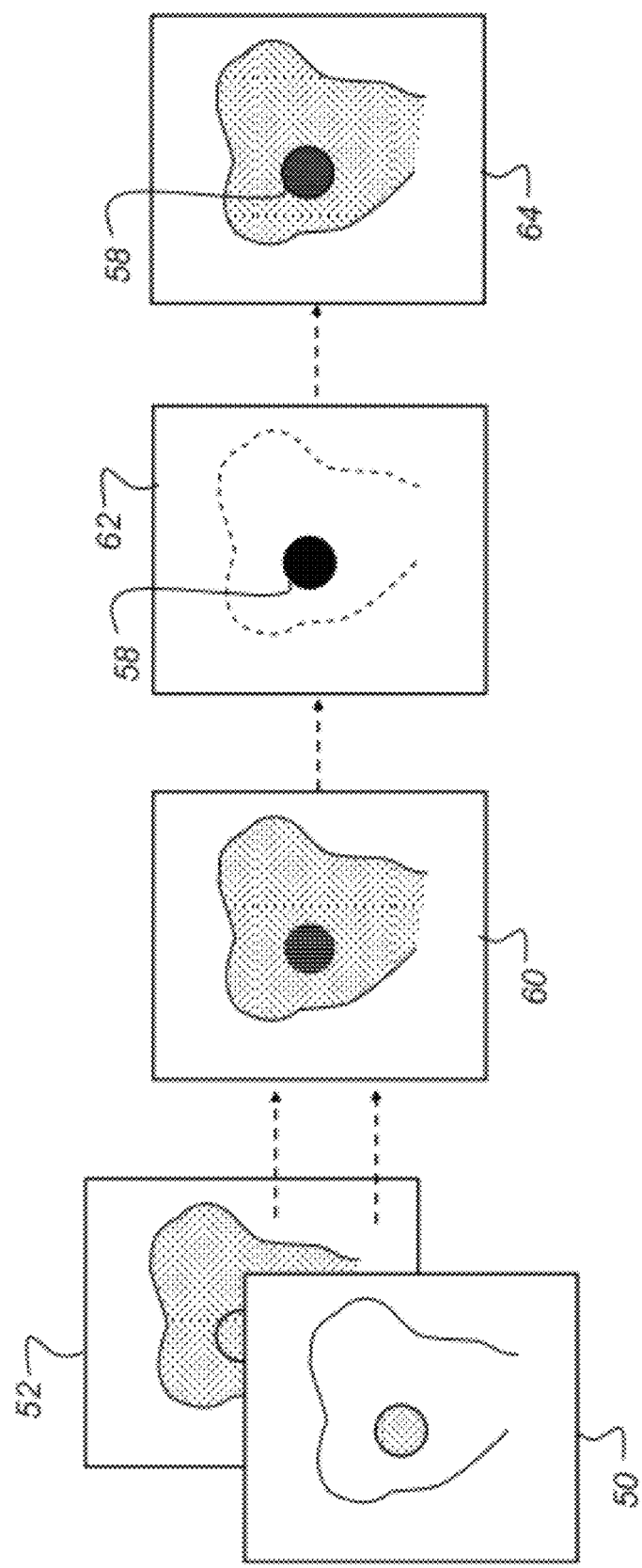
FIG. 7 is a block diagram showing a sequence of image processing for generating an enhanced threshold image according to one embodiment.

Following an initial combination of fluorescence and reflectance values, additional image processing may also be of benefit. A thresholding operation, executed using image processing techniques familiar to those skilled in the imaging arts, or some other suitable conditioning of the combined image data used for FIRE image 60, may be used to further enhance the contrast between a carious region and sound tooth structure. Referring to FIG. 7, there is shown, in block diagram form, a sequence of image processing for generating an enhanced threshold FIRE image 64 according to one embodiment. Fluorescence image 50 and reflectance image 52 are first combined to form FIRE image 60, as described previously. A thresholding operation is next performed, providing threshold image 62 that defines more clearly the area of interest, carious region 58. Then, threshold image 62 is combined with original FIRE image 60 to generate enhanced threshold FIRE image 64. Similarly, the results of threshold detection can also be superimposed onto a white light image 54 (FIG. 6) in order to definitively outline the location of a carious infection.

It can be readily appreciated that any number of complex image processing algorithms could alternately be used for combining the reflectance and fluorescence image data in order to obtain an enhanced image that identifies carious regions more clearly. It may be advantageous to apply a number of different imaging algorithms to the image data in order to obtain the most useful result. In one embodiment, an operator can elect to use any of a set of different image processing algorithms for conditioning the fluorescence and reflectance image data obtained. This would allow the operator to check the image data when processed in a number of different ways and may be helpful for optimizing the detection of carious lesions having different shape-related characteristics or that occur over different areas of the tooth surface.

It is emphasized that the image contrast enhancement achieved in the present invention, because it employs both reflectance and fluorescence data, is advantaged over conventional methods that use fluorescent image data only. Conventionally, where only fluorescence data is obtained, image processing has been employed to optimize the data, such as to transform fluorescence data based on spectral response of the camera or of camera filters or other suitable characteristics. For example, the method of the '2356 Stookey et al. disclosure, cited above, performs this type of optimization, transforming fluorescence image data based on camera response. However, these conventional approaches overlook the added advantage of additional image information that the back-scattered reflectance data obtains.

Alternate Embodiments

The method of the present invention admits a number of alternate embodiments. For example, the contrast of either or both of the reflectance and fluorescence images may be improved by the use of a polarizing element. It has been observed that enamel, having a highly structured composition, is sensitive to the polarization of incident light. Polarized light has been used to improve the sensitivity of dental imaging techniques, for example, in "Imaging Caries Lesions and Lesion Progression with Polarization Sensitive Optical Coherence Tomography" in *J. Biomed Opt.*, 2002 October; 7(4): pp. 618-627, by Fried et al.

Specular reflection tends to preserve the polarization state of the incident light. For example, where the incident light is s-polarized, the specular reflected light is also s-polarized. Backscattering, on the other hand, tends to de-polarize or randomize the polarization of the incident light. Where incident light is s-polarized, back-scattered light has both s- and p-polarization components. Using a polarizer and analyzer, this difference in polarization handling can be employed to help eliminate unwanted specular reflectance from the reflectance image, so that only back-scattered reflectance is obtained.

Figure 24:
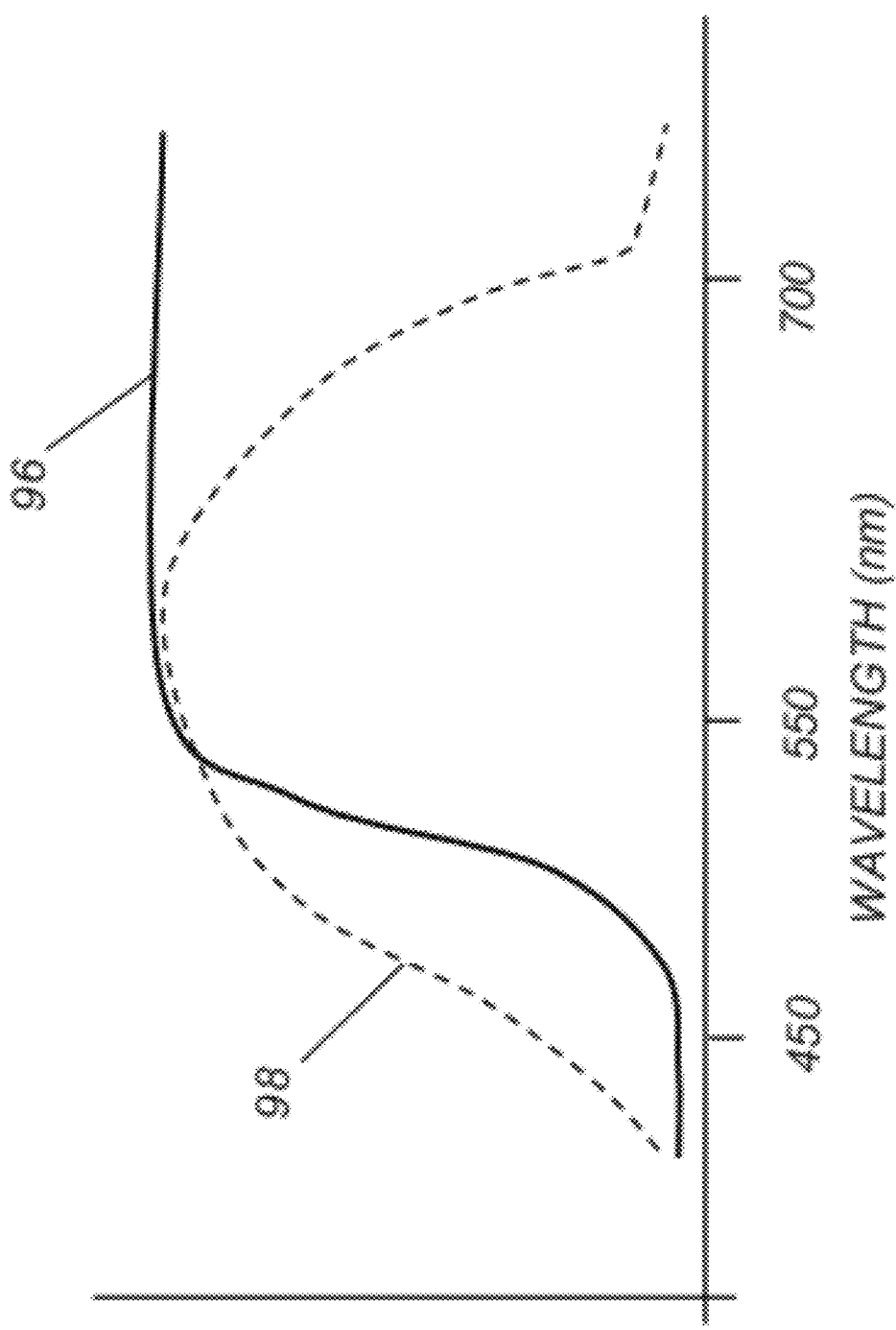
FIG. 24 is a graph showing characteristic curves for white light and for a long pass filter used in the apparatus of the present invention.

Referring to FIG. 4A, there is shown an embodiment of imaging apparatus 10 that expands upon the basic model shown in FIGS. 1-3, employing a polarizer 42 in the path of the incident illumination light and other supporting optics. Polarizer 42 transmits linearly polarized incident light. An optional analyzer 44 may also be provided in the return path of image-bearing light from tooth 20 as a means to minimize the specular reflectance component. With this polarizer 42/analyzer 44 combination as polarizing elements, reflectance light in the return path and sensed by camera 30 or 32 is predominantly back-scattered light, that portion of the reflectance that is desirable for combination with the fluorescence image data according to the present invention. A long-pass filter 15 in the path of returned light from the tooth is used to attenuate ultraviolet and shorter wavelength visible light (for example, light over the blue portion of the spectrum, centered near about 405+/−40 nm) and to pass longer wavelength light. This arrangement minimizes the effect of blue light that may be used to excite fluorescence (normally centered in the green portion of the spectrum, nominally about 550 nm) and, by attenuating this shorter-wavelength light, allows the use of a white light source as light source 12 for obtaining a reflectance image. The curves of FIG. 24 show the overall relationship between a white light curve 98 (shown with a dashed line) and a long-pass filter curve 96.

Figure 4C:
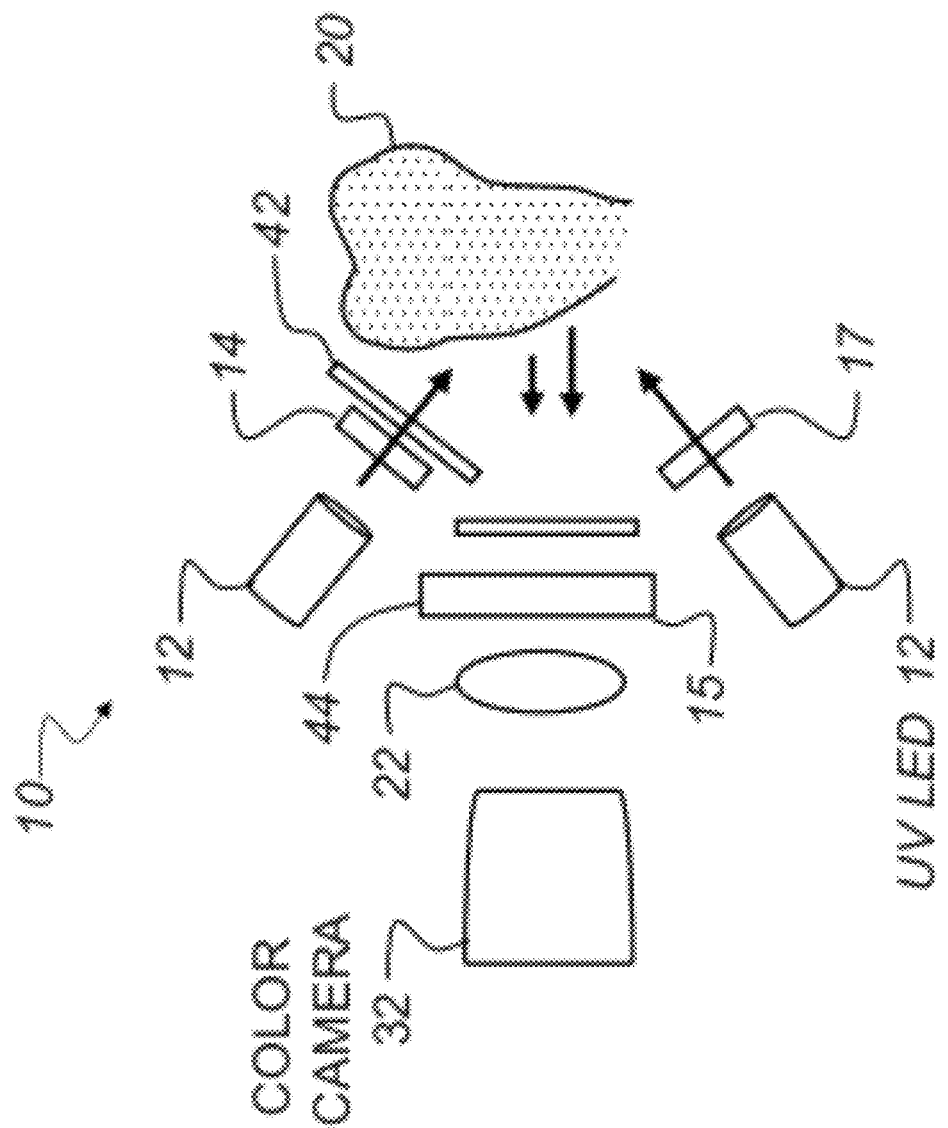
FIG. 4C is a schematic block diagram of an alternate embodiment using a band pass filter with a narrow band light source.

FIG. 4C shows an alternate embodiment using multiple light sources 12, each light source 12 having a different spectral range. Here, one light source 12 is a white light source for obtaining the reflectance image. The typical spectral range for a white light source can include wavelengths from about 400 to about 700 nm. The other light source 12 is a UV LED or other source that emits light having shorter wavelengths for exciting fluorescent emission. For example, its spectral range may be well within 300-500 nm. A band pass filter 17 can be used to narrow the band and reduce optical crosstalk from this second light source into the fluorescence image.

Where there are multiple light sources 12, individual light sources 12 can be toggled on and off in order to obtain the corresponding reflectance or fluorescence image at any one time. For the embodiment described with reference to FIG. 4C, for example, white light source 12 is on to obtain the reflectance image (or white light image) at camera 32 or other sensor. The other UV LED source is off. Then, when white light source 12 is turned off and the UV LED source is energized, a fluorescence image can be obtained.

Figure 25:
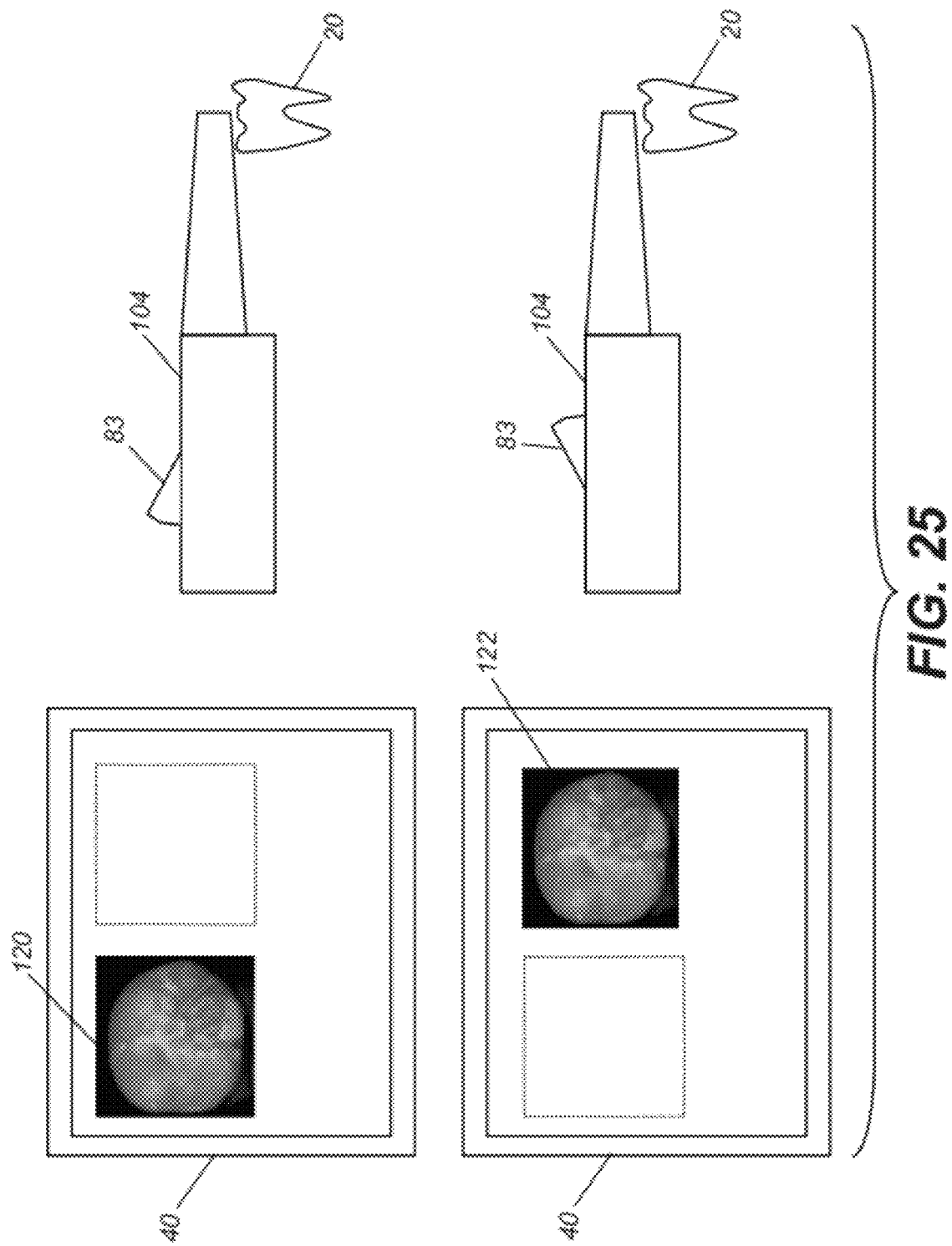
FIG. 25 is a diagram showing operation of a toggle switch for obtaining separate images.

FIG. 25 shows an embodiment with an imaging probe 104 having a toggle switch 83 and the corresponding display 40 for each position of toggle switch 83. In one position, as shown in the upper portion of FIG. 25, toggle switch 83 enables capture of fluorescence image 120. In another position, shown in the lower portion of FIG. 25, toggle switch 83 enables capture of reflectance image 122.

In an alternate embodiment, toggling in this fashion can be accomplished automatically, such as by control logic circuitry in communication with camera 32 or sensor in imaging apparatus 10. This arrangement allows a single camera 32 or other sensor to obtain images of different types.

An alternate embodiment, shown in FIG. 4B, employs a polarizing beamsplitter 18 (sometimes termed a polarization beamsplitter) as a polarizing element. In this arrangement, polarizing beamsplitter 18 advantageously performs the functions of both the polarizer and the analyzer for image-bearing light, thus offering a more compact solution. Tracing the path of illumination and image-bearing light shows how polarizing beamsplitter 18 performs this function. Illumination from light source 12 is essentially unpolarized. Polarizing beamsplitter 18 transmits p-polarization, as shown by the dotted arrow in FIG. 4B, and reflects s-polarization, directing this light to tooth 20. At the tooth 20, back-scattering depolarizes this light. Polarizing beamsplitter 18 treats the back-scattered light in the same manner, transmitting the p-polarization and reflecting the s-polarization. The resulting p-polarized light can then be filtered at long-pass filter 15, and detected at camera 30 (with suitable color filter as was described with reference to FIG. 1) or color camera 32. Because specular reflected light is s-polarized, polarizing beamsplitter 18 effectively removes this specular reflective component from the light that reaches camera 30, 32.

Polarized illumination results in further improvement in image contrast, but at the expense of light level, as can be seen from the description of FIGS. 4A and 4B. Hence, when using polarized light in this way, it may be necessary to employ a higher intensity light source 12. This employment of polarized illumination is particularly advantaged for obtaining the reflectance image data and is also advantaged when obtaining the fluorescence image data, increasing image contrast and minimizing the effects of specular reflection.

One type of polarizer 42 that has particular advantages for use in imaging apparatus 10 is the wire grid polarizer, such as those available from Moxtek Inc. of Orem, Utah and described in U.S. Pat. No. 6,122,103 (Perkins et al.) The wire grid polarizer exhibits good angular and color response, with relatively good transmission over the blue spectral range. Either or both polarizer 42 and analyzer 44 in the configuration of FIG. 4A could be wire grid polarizers. Wire grid polarizing beamsplitters are also available, and can be used in the configuration of FIG. 4B.

The method of the present invention takes advantage of the way the tooth tissue responds to incident light of sufficient intensity, using the combination of fluorescence and light reflectance to indicate carious areas of the tooth with improved accuracy and clarity. In this way, the present invention offers an improvement upon existing non-invasive fluorescence detection techniques for caries. As was described in the background section given above, images that have been obtained using fluorescence only may not clearly show caries due to low contrast. The method of the present invention provides images having improved contrast and is, therefore, of more potential benefit to the diagnostician for identifying caries.

In addition, unlike earlier approaches using fluorescence alone, the method of the present invention also provides images that can be used to detect caries in its very early incipient stages. This added capability, made possible because of the perceptible back-scattering effects for very early carious lesions, extends the usefulness of the fluorescence technique and helps in detecting caries during its reversible stages, so that fillings or other restorative strategies might not be needed.

Figure 9:
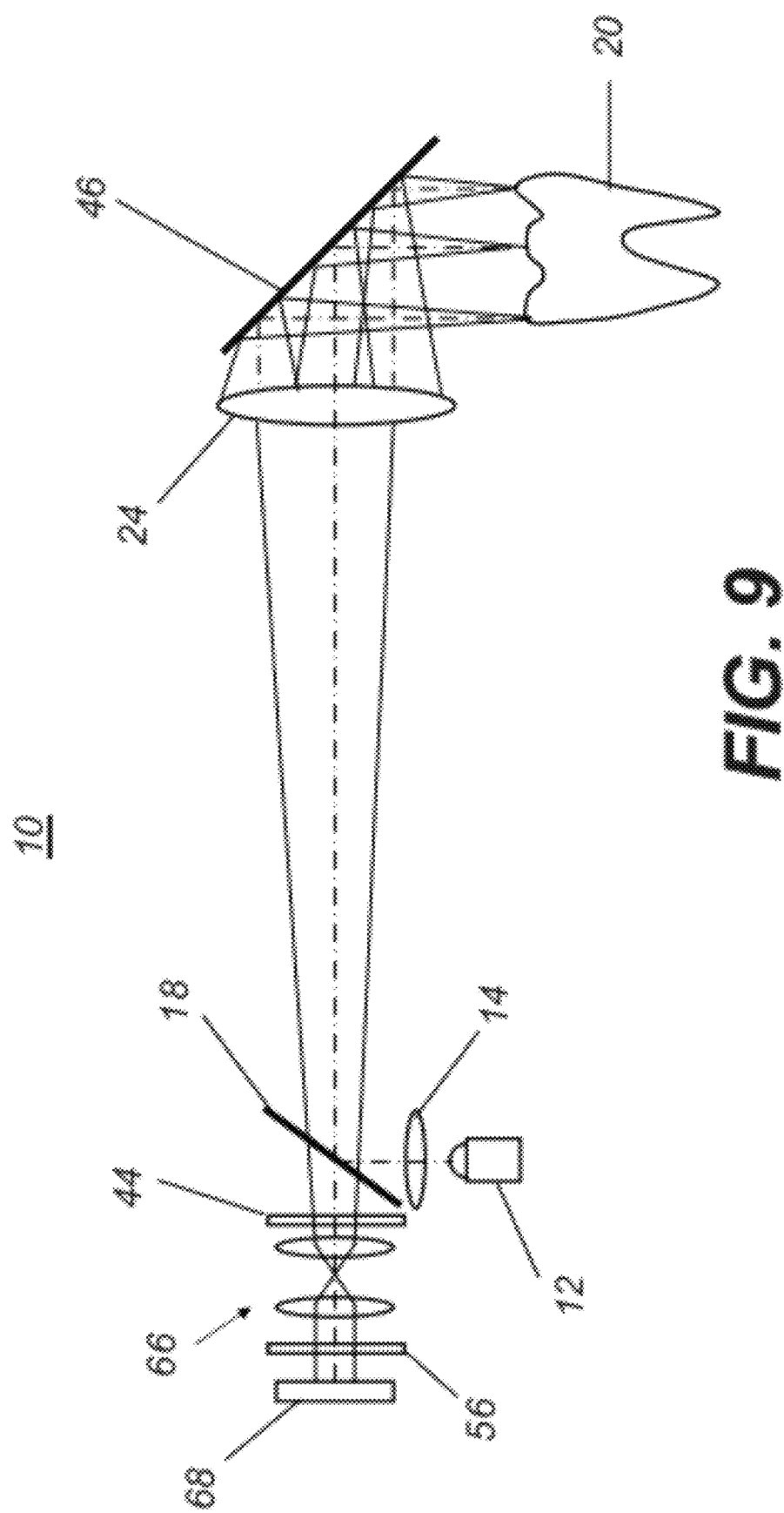
FIG. 9 is a schematic block diagram of an imaging apparatus for caries detection using polarized light in one embodiment of the present invention.

Referring to FIG. 9, there is shown an embodiment of imaging apparatus 10 using polarized light from a polarizing beamsplitter 18 and using a telecentric field lens 24. Light source 12, typically a light source in the blue wavelength range for exciting maximum fluorescence from tooth 20 provides illumination through lens 14 and onto polarizing beamsplitter 18. Here, one polarization state transmits, the other is reflected. In a typical embodiment, p-polarized light is transmitted through polarizing beamsplitter 18 and is, therefore, discarded. The s-polarized light is reflected toward tooth 20, guided by field lens 24 and an optional turning mirror 46 or other reflective surface. Light returning from tooth 20 can include a specular reflection component and a back-scattered reflection component. Specular reflectance does not change the polarization state. Thus, for the s-polarized illumination, that is, for the unwanted specularly reflected component, the reflected light is directed back toward light source 12. As has been observed, back-scattered reflectance undergoes some amount of depolarization. Thus, some of the back-scattered reflected light has p-polarization and is transmitted through polarizing beamsplitter 18. This returning light may be further conditioned by optional analyzer 44 and then directed by an imaging lens 66 to sensor 68, such as a camera, through color filter 56. Long pass filtering (not shown in FIG. 9) could also be employed in the path of light returned from tooth 20. Color filter 56 is used in this arrangement to block light from the light source that was used to excite fluorescence, since the response of the color filter array (CFA) built inside the sensor is typically not sharp enough to block the light from the light source in this region. In this way, the returning light directed to sensor 68 is fluorescence only.

Figure 10:
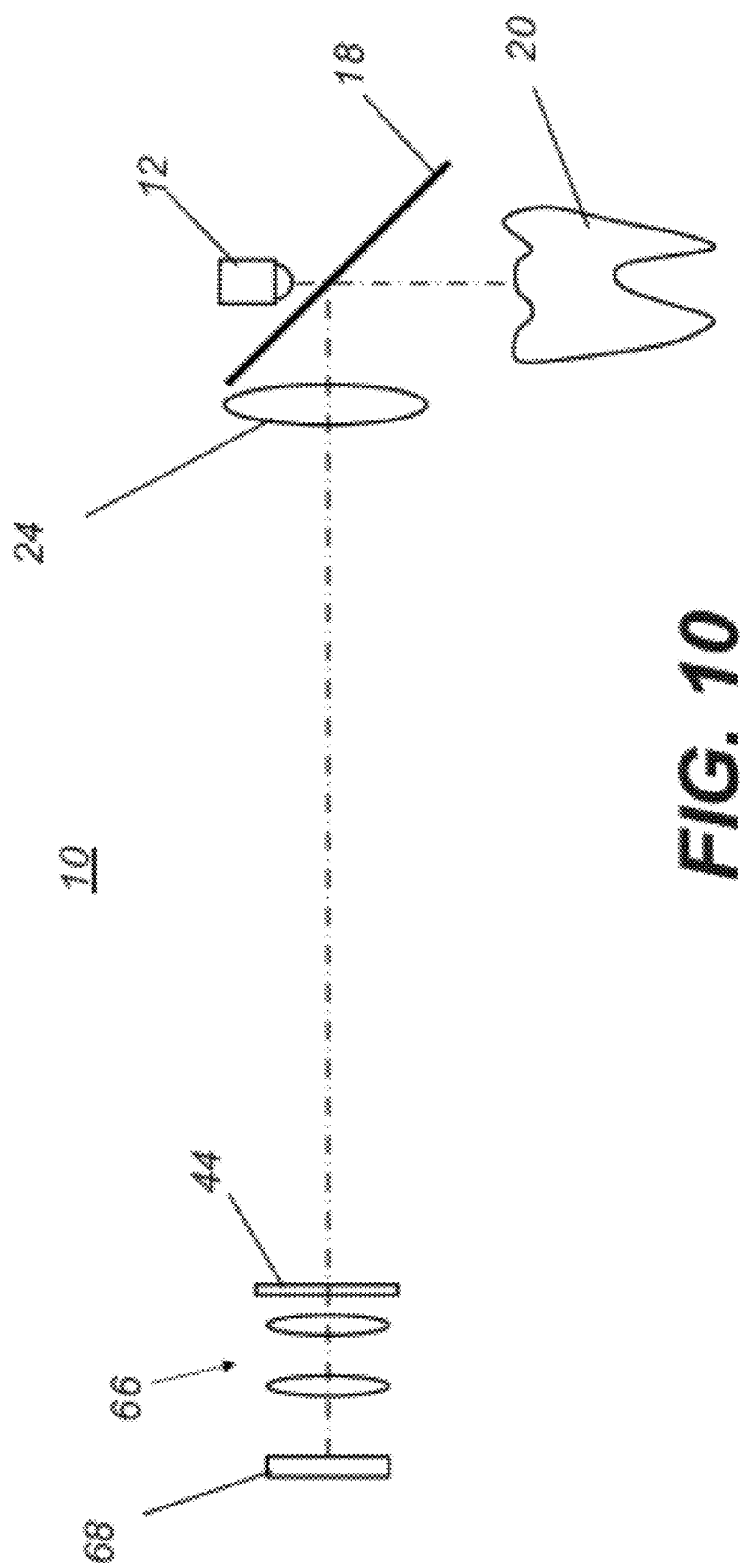
FIG. 10 is a schematic block diagram of an imaging apparatus for caries detection using polarized light in an alternate embodiment of the present invention.

The use of telecentric field lens 24 is advantaged in the embodiment of FIG. 9. Telecentric optics provides constant magnification within the depth of field, which is particularly useful for highly contoured structures such as teeth that are imaged at a short distance. Perspective distortion is minimized. Telecentric field lens 24 could be a multi-element lens, represented by a single lens symbol in FIG. 9. Light source 12 may be any suitable color, including white, blue, green, red, or near infrared, for example. Light source 12 may also be a more complex assembly capable of providing light at different spectral bands, such as through the use of movable color filters. FIG. 10 shows an alternate embodiment of imaging apparatus 10 in which no turning mirror is used. Instead, polarizing beamsplitter 18 is disposed in the imaging path between field lens 24 and tooth 20. Alternately, if no field lens is used, polarizing beamsplitter 18 is disposed in the imaging path just before tooth 20. Light source 12 is positioned to direct illumination through polarizing beamsplitter 18, so that the illumination effectively bypasses field lens 24 if any. Specularly reflected light is again discarded by means of polarizing beamsplitter 18 and analyzer 44.

Figure 11:
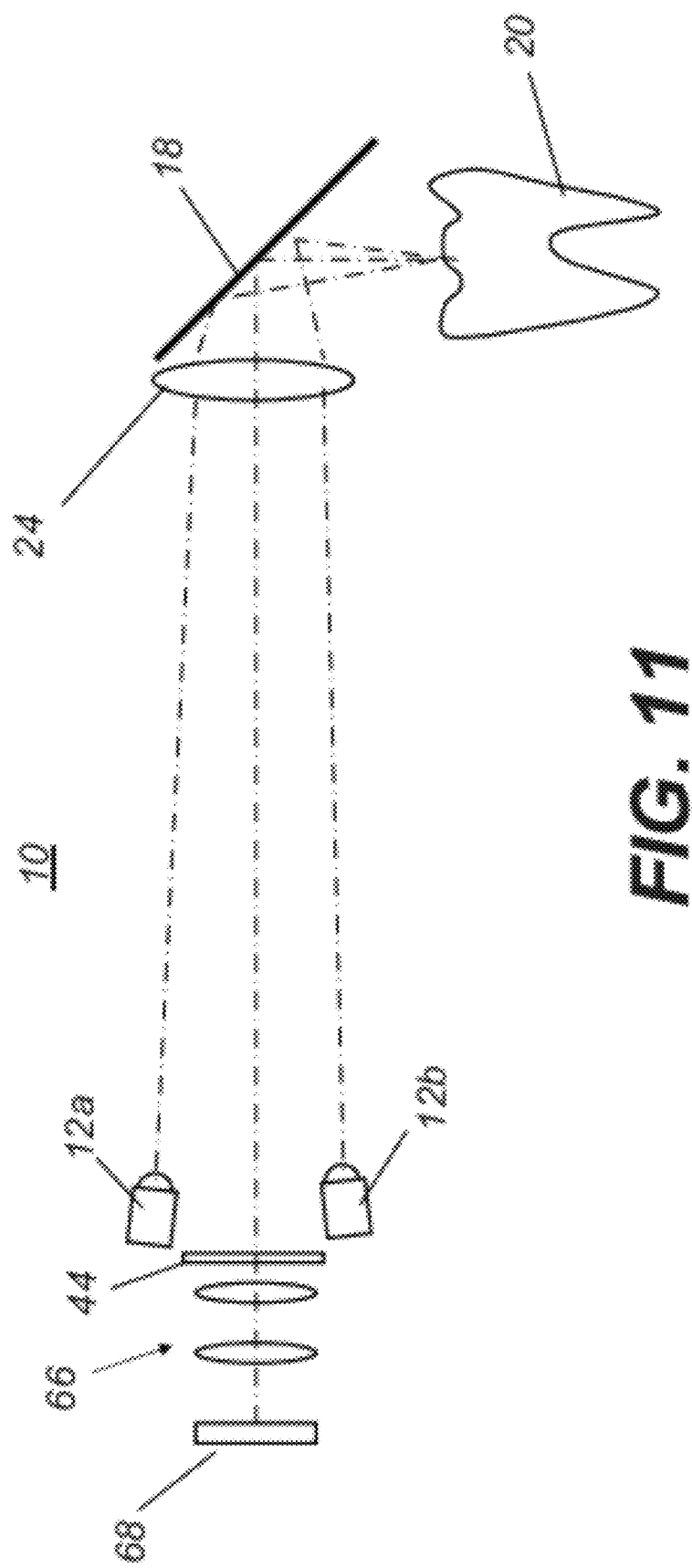
FIG. 11 is a schematic block diagram of an imaging apparatus for caries detection using polarized light in an alternate embodiment of the present invention.

The block diagram of FIG. 11 shows an alternate embodiment of imaging apparatus 10 in which two separate light sources 12a and 12b are used. Light sources 12a and 12b may both emit the same wavelengths or may emit different wavelengths. They may illuminate tooth 20 simultaneously or one at a time. Polarizing beamsplitter 18 is disposed in the imaging path between field lens 24 and tooth 20, thus providing both turning and polarization functions.

FIG. 12A shows another alternate embodiment, similar to that shown in FIG. 11, in which each of light sources 12a and 12b has a corresponding polarizer 42a and 42b. A turning mirror could be substituted for polarizing beamsplitter 18 in this embodiment; however, the use of both polarized illumination, as provided from the combination of light sources 12a and 12b and their corresponding polarizers 42a and 42b, and polarizing beamsplitter 18 can be advantageous for improving image quality. FIG. 12B is another embodiment with additional LEDs to increase the light level on the tooth or other object. As described above, the LEDs can be white light LEDs and/or blue LEDs. In order to achieve uniform illumination, the arrangement of LEDs, with respect to the tooth or other object, should be symmetric.

FIG. 12C is another embodiment with an alternate illumination implementation. In this embodiment, fiber bundles are used to direct light from LEDs or other light source to the tooth or other object. In FIG. 12C, four optical fiber bundles 49a-49d are used. Fiber bundles 49a and 49b are used to deliver white light to the object. Two polarizers 42a and 42b are placed in front of the output surface of optical fiber bundles 49b, 49d to create linear polarized illumination. Fiber bundles 49c and 49d couple the light from Blue or UV LEDs or other light sources to excite the fluorescence from the object.

Figure 19:
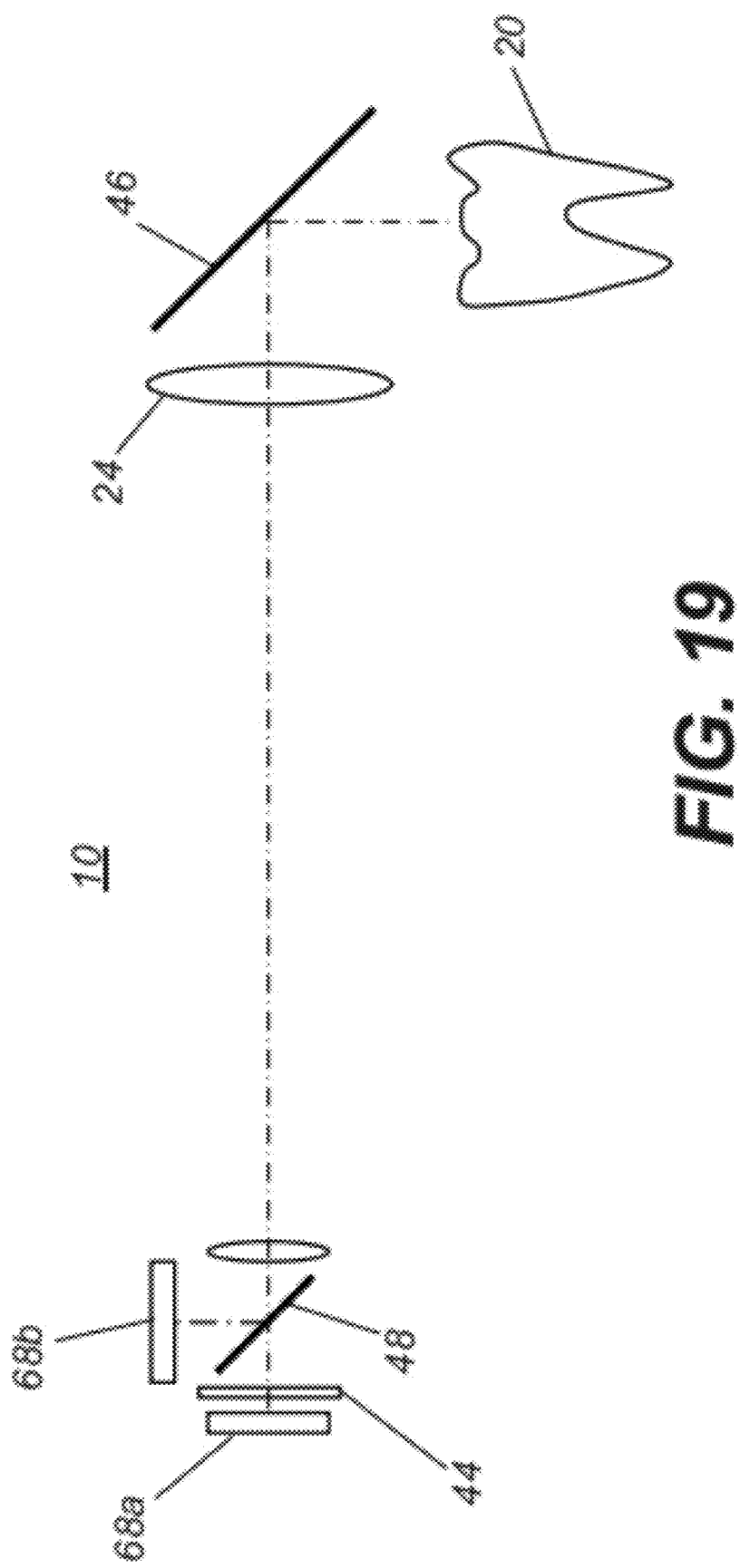
FIG. 19 is a block diagram of an alternate embodiment for the imaging probe with two sensors.

FIG. 19 is an alternate embodiment for the imaging probe with two sensors 68a and 68b. One dichroic mirror 48 is used as a spectral separator in this embodiment to direct the reflected light with different spectral bands to two different sensors. For example, in one embodiment, dichroic mirror 48 transmits light within the visible spectrum (440 nm to 650 nm) and reflects UV (<400 nm) and NIR (>700 nm). With this embodiment, the imaging probe can also be employed in other applications, such as for tooth color shade matching and for soft tissue imaging, for example.

In one embodiment, the apparatus displays a fluorescence image, instead of a white light image, as the live video image. This enables the operator to screen the tooth for caries detection using fluorescence imaging and to assess tooth condition using the white light image for other applications. One switch is necessary, either in the probe or in the software, so that the user can select the live video image mode based on the application. The switch in the probe can be a two-step button switch. Without pressing the button switch, the live video image is a white light image. When the button is pressed to its half way travel position, the fluorescence image becomes the live video image. Both fluorescence and white light images can be captured and saved when the button is pressed to its full travel position.

With high-speed electronics and software, two live video images can be displayed in the monitor to the user. Both single-sensor and dual-sensor configurations can be used to display two live video images. In order to obtain two live images and avoid crosstalk, the LEDs with different wavelengths need to be switched alternately on and off. An advantage in displaying two live video images is that the user can compare the fluorescence and white light image and diagnose suspicious regions of these images. Using image processing utilities described subsequently, a suspicious region can be highlighted automatically when the fluorescence and white image are alternately obtained.

Figure 21:
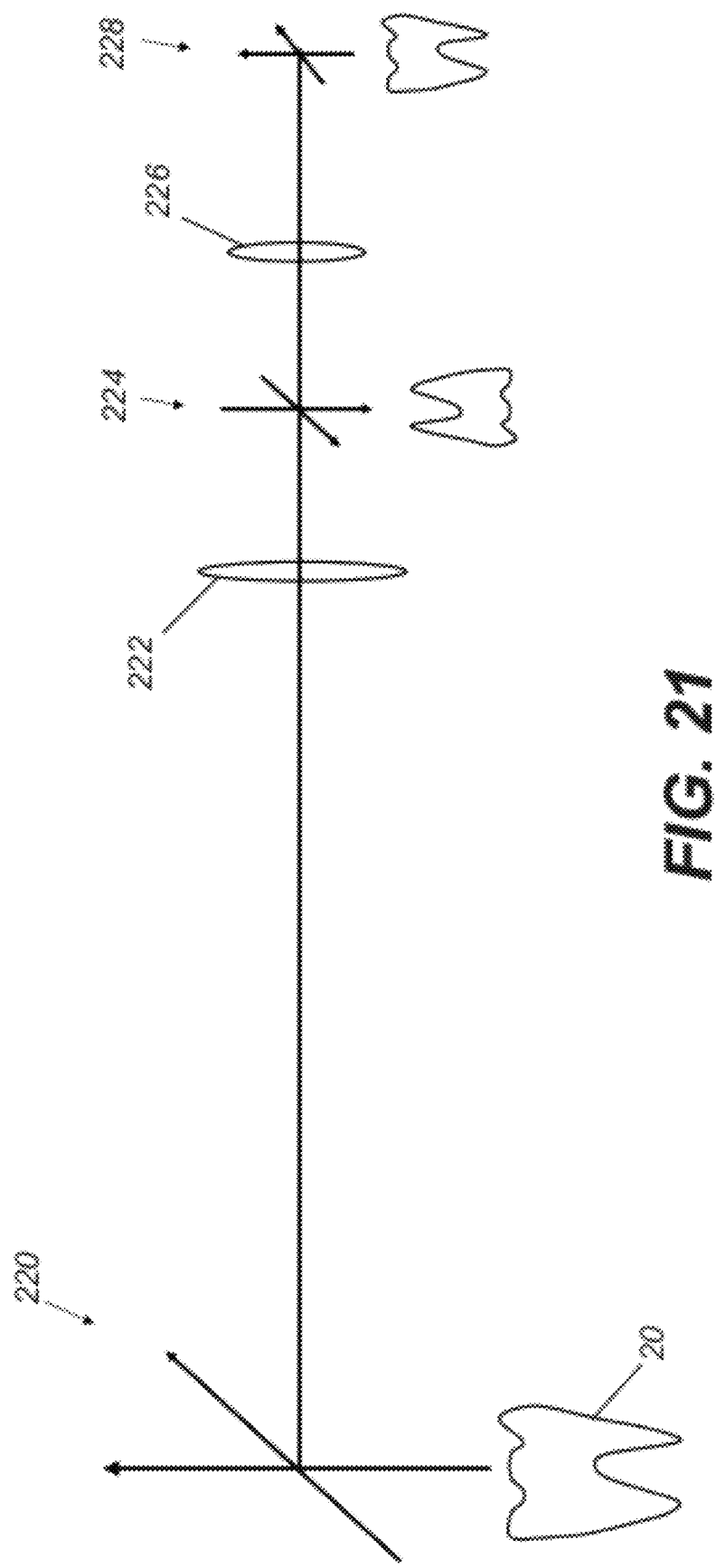
FIG. 21 is a block diagram showing an image relay arrangement used in one embodiment.

One common difficulty with conventional intra-oral cameras and caries detection image devices is that the live video image moves in the direction opposite to probe movement. This is due to imaging lens properties: the image is reversed when using only one imaging lens. Several optical methods can be applied to form the image. One of the methods is to use an image relay technique, as shown in FIG. 21. Image lens 222 forms an intermediate image 224 of the object, tooth 20. The orientation of intermediate image 224 is opposite to the object 220. An image lens 226 then forms a final image 228 of intermediate image 224. The orientation of image 228 is the same as the object, tooth 20. Using this embodiment, the moving direction of the final image 228 will be the same as the probe movement. In addition, folding mirrors can be used to change image orientation as necessary. Even without such extra optical components to change image orientation, software can manipulate the image to correct the image orientation that is displayed to the user.

Figure 23A:
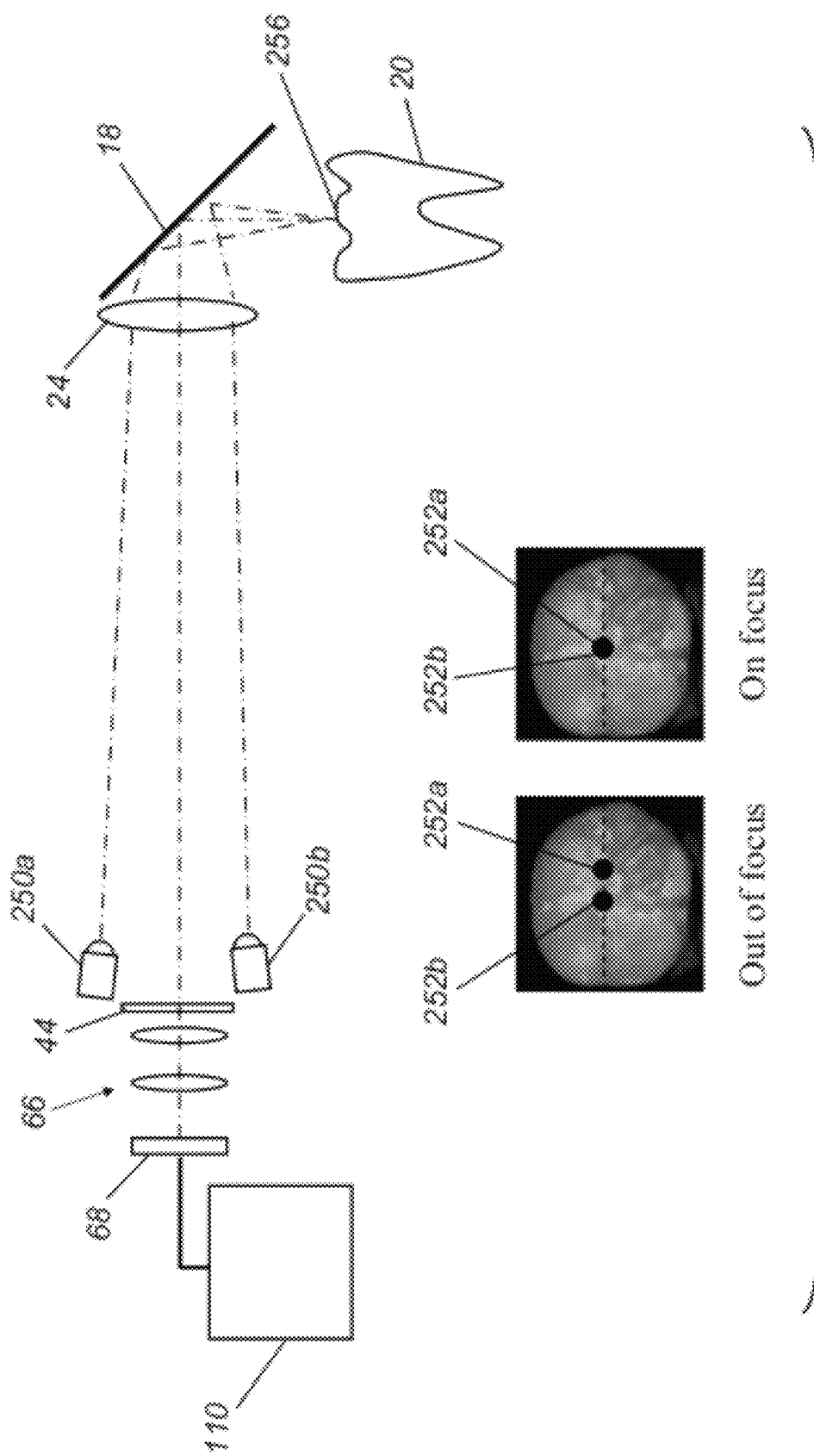
FIGS. 23A and 23B are block diagrams of embodiments for image capture with auto-focusing capability.
Figure 23B:
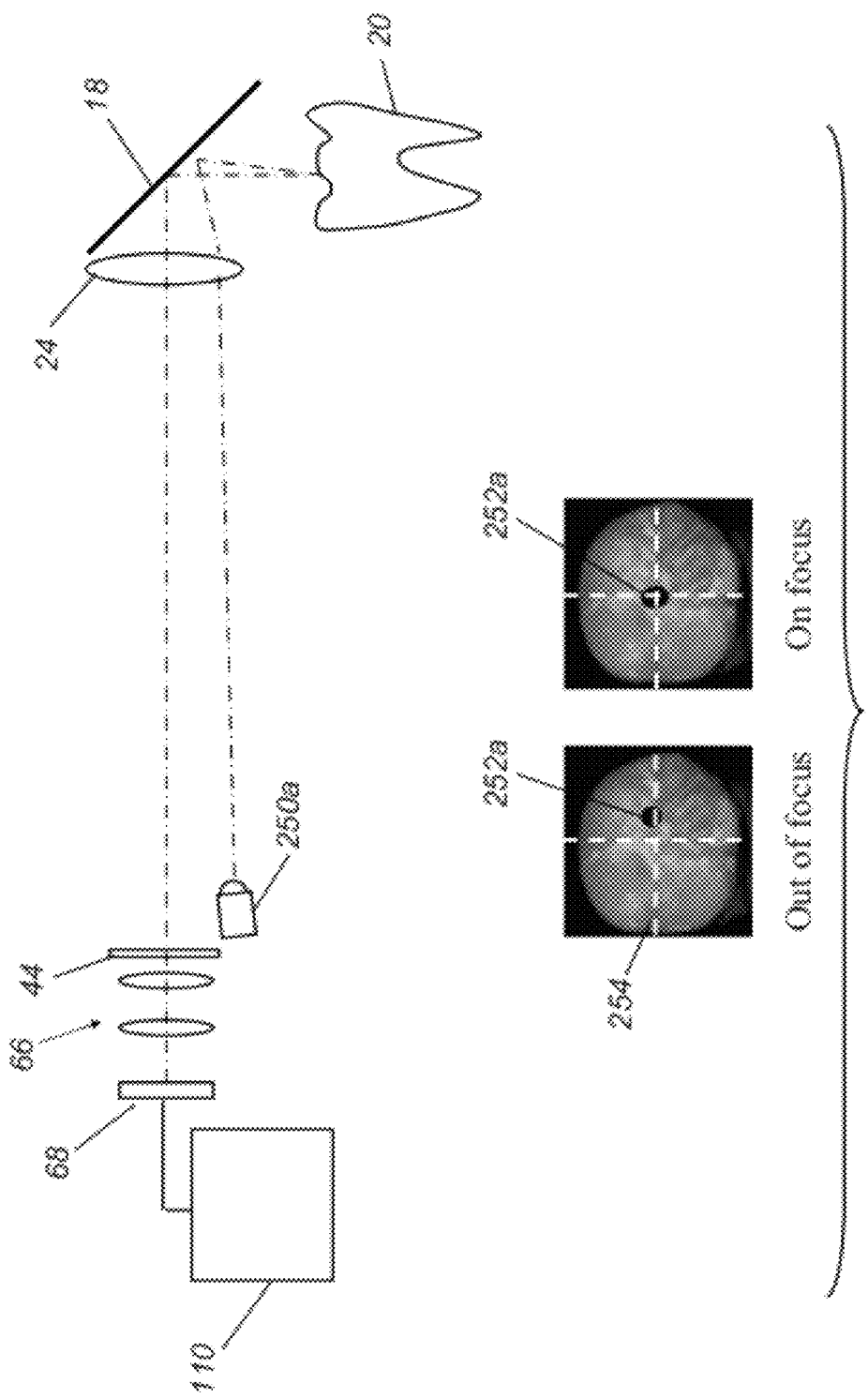

FIGS. 23A and 23B are two embodiments for image capture with auto-focusing capability. For simplicity, white light LEDs and LEDs for fluorescence imaging are not shown in FIGS. 23A and 23B. Light sources 250a and 250b are LEDs with integral lenses. Collimating lenses in light sources 250a and 250b form images 252a and 252b, respectively, onto a cross point 256 of the object plane and optical axis. As shown in FIG. 23A, when the probe is not in the right position (indicating focus), images 252a and 252b do not overlap. FIG. 23C shows how this is implemented in one embodiment, with tooth 20 at different positions relative to cross point 256. At left in this figure, tooth 20 is beyond cross point 256, thus out of focus. At right, tooth 20 is within cross point 256, also out of focus. In the central portion of this figure, tooth 20 is positioned within focus. To achieve focus with this arrangement, the operator simply moves the probe so that images 252a and 252b overlap. When images 252a and 252b overlap, the user can instruct the system to take the images. As an alternative embodiment, auto focus can be provided. Software working with or within control circuitry 110 can detect and track the positions of images 252a and 252b, using light detection techniques familiar to those skilled in the imaging arts. The software can then trigger sensor 68 or the camera to take the images once images 252a and 252b overlap.

FIG. 23B is a simplified version of FIG. 23A. In this configuration, only one LED and lens 250a is used. A crosshair 254 displays on the monitor to indicate the center of the image and the optical axis. When images 252a align with crosshair 254, the probe is on focus. If software is applied to track the position of image 252a, the use of crosshair 254 or similar feature is not required.

Embodiments Using Optical Coherence Tomography (OCT)

Optical coherence tomography (OCT) is a non-invasive imaging technique that employs interferometric principles to obtain high resolution, cross-sectional tomographic images of internal microstructures of the tooth and other tissue that cannot be obtained using conventional imaging techniques. Due to differences in the backscattering from carious and healthy dental enamel OCT can determine the depth of penetration of the caries into the tooth and determine if it has reached the dentin enamel junction. From area OCT data it is possible to quantify the size, shape, depth, and determine the volume of carious regions in a tooth.

In an OCT imaging system for living tissue, light from a low-coherence source, such as an LED or other light source, can be used. This light is directed down two different optical paths: a reference arm of known length and sample arm, which goes to the tooth. Reflected light from both reference and sample arms is then recombined, and interference effects are used to determine characteristics of the underlying features of the sample. Interference effects occur when the optical path lengths of the reference and sample arms are equal within the coherence length of the light source. As the path length difference between the reference arm and the sample arm is changed the depth of penetration in the sample is modified in a similar manner. Typically in biological tissues NIR light of around 1300 nm can penetrate about 3-4 mm as is the case with dental tissue. In a time domain OCT system the reference arm delay path relative to the sample arm delay path is alternately increased monotonically and decreased monotonically to create depth scans at a high rate. To create a 2-dimensional scan the sample measurement location is changed in a linear manner during repetitive depth scans such as with a galvanometer.

Figure 13:
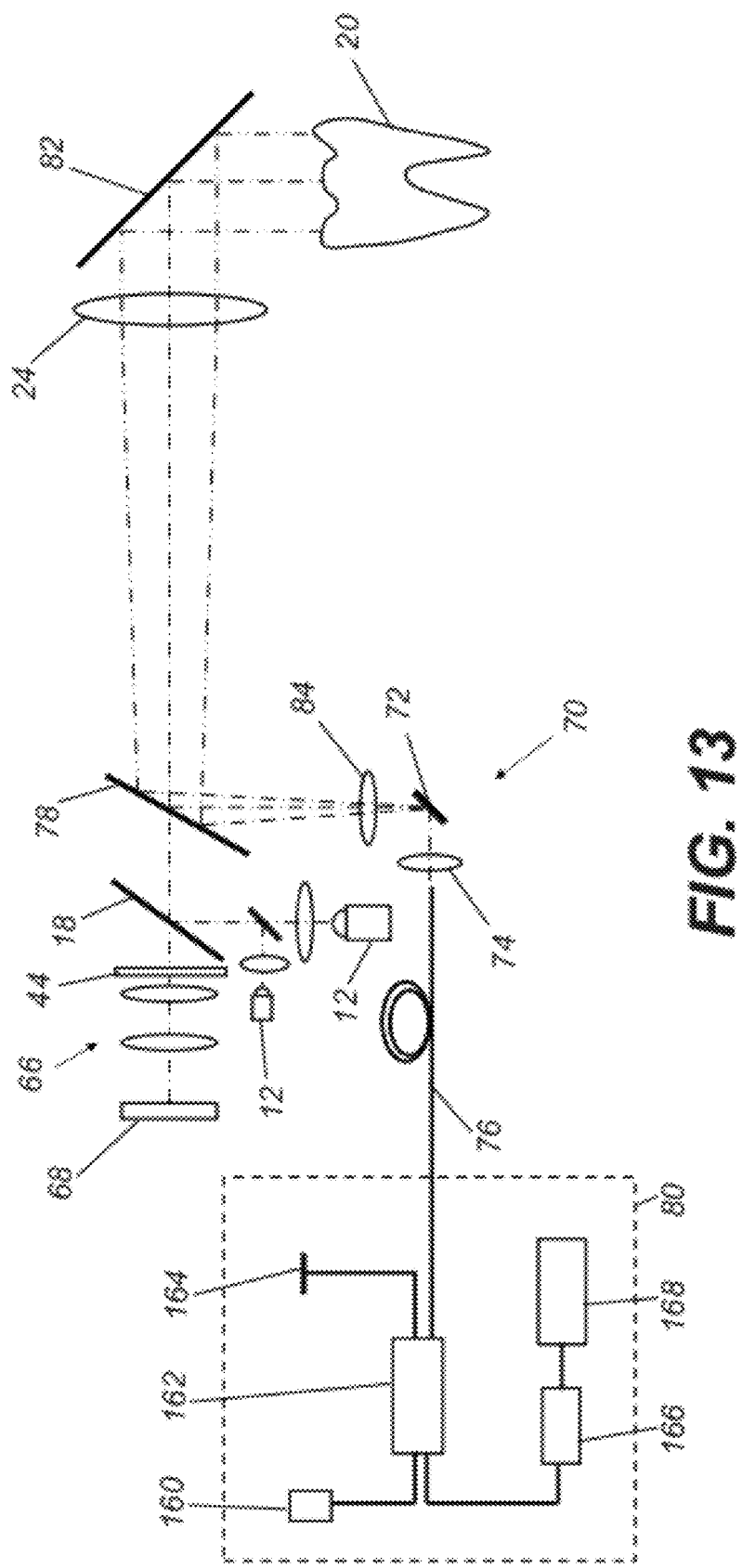
FIG. 13 is a schematic block diagram of an imaging apparatus for caries detection using polarized light and OCT scanning in one embodiment.

In an OCT system 80 shown in FIG. 13, light from a low-coherence light source 160, such as an LED or other light source, can be used. This light is split and made to travel down two different optical paths being a reference arm 164 with a built in reference delay scanner to alternately change its path length and a sample arm 76 that goes to the tooth by a beamsplitting and combining element 162. Reflected light from both reference and sample arms is then recombined by beamsplitting and combining element 162, and interference effects are used to determine characteristics of the underlying features of the sample. The reference arm and sample arm pathlengths are made to be the same at some part of the reference delay scanning operation to enable observation of interference effects. The recombined and interfering light from beamsplitting and combining element 162 is then sent to a detector and processing electronics 166 where the optical interference signal is converted to an electrical signal which is then acquired by data acquisition hardware and computer system 168 for further processing and display. The optical elements of OCT system 80 are configured as an interferometer.

Still referring to FIG. 13, there is shown an embodiment of imaging apparatus 10 using both FIRE imaging methods and OCT imaging. Light source 12, polarizing beamsplitter 18, field lens 24, a turning mirror 82, imaging lens 66, and sensor 68 provide the FIRE imaging function along an optical path as described previously. An OCT imager 70 directs light for OCT scanning into the optical path that is shared with the FIRE imaging components. Light from OCT system 80 is directed through a sample arm 76 and through a collimating lens 74 to a scanning element 72, such as a galvanometer, for example. A dichroic mirror 78 is transmissive to visible light and reflective for near-IR and longer wavelengths. This sample arm light is then directed from dichroic mirror 78 to tooth 20 through the optical system that includes a scanning lens 84 and field lens 24. Field lens 24 is not required for non-telecentric OCT scanning. Returned light from tooth 20 travels the same optical path and is recombined with light from the reference arm of interferometer 162.

OCT scans are 2-dimensional in the plane of the impinging beam. Image-forming logic combines adjacent lines of successive 2-dimensional scans (length along the galvanometer scan line and depth) to form a multi-dimensional volume image of the sample (tooth) structure, including portions of the tooth that lie beneath the surface.

For OCT imager 70, the light provided is continuous wave low coherence or broadband light, and may be from a source such as a super luminescent diode, diode-pumped solid-state crystal source, or diode-pumped rare earth-doped fiber source, for example. In one embodiment, near-IR light is used, such as light having wavelengths near 1310 nm, for example.

Figure 14B:
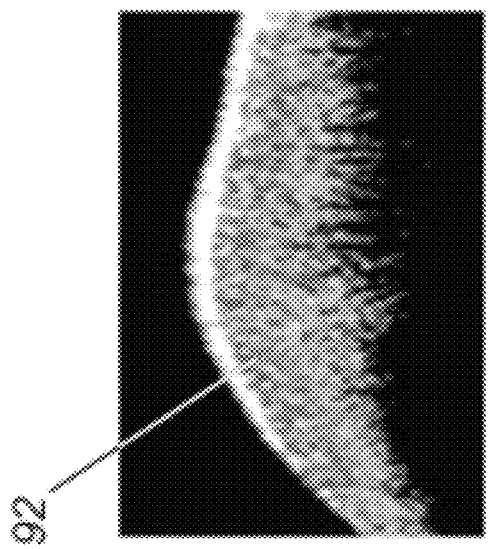
FIG. 14A is a plan view of an operator interface screen in one embodiment.
FIG. 14 B is an example display of OCT scanning results.
Figure 14A:
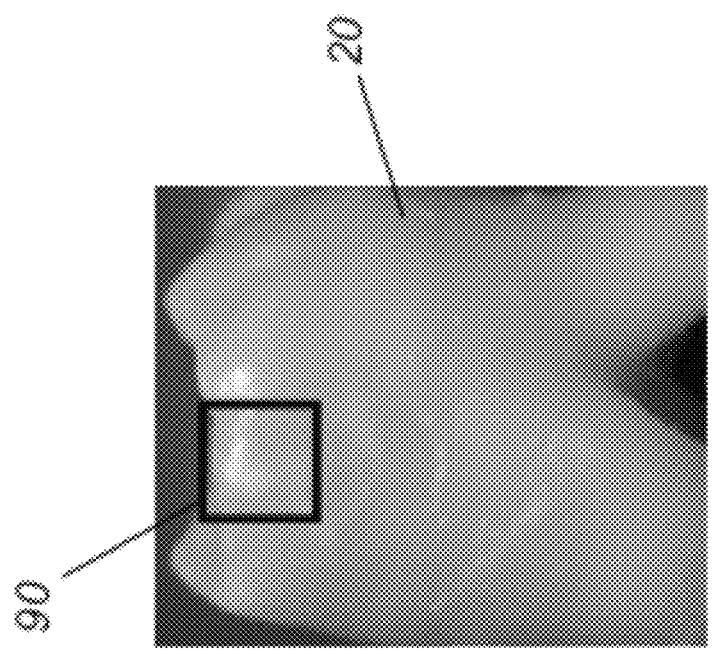

While the OCT scan is a particularly powerful tool for helping to show the condition of the tooth beneath the surface, it can be appreciated that this type of detailed information is not needed for every tooth or for every point along a tooth surface. Instead, it would be advantageous to be able to identify specific areas of interest and apply OCT imaging to just those areas. Referring to FIG. 14A, there is shown a display of tooth 20. An area of interest 90 can be identified by a diagnostician for OCT scanning. For example, using operator interface tools at processing apparatus 38 and display 40 (FIGS. 1-3), an operator can outline area of interest 90 on display 40. This could be done using a computer mouse or some type of electronic stylus as a pointer, for example. The OCT scan can then be performed when a probe or other portion of imaging apparatus 10 of FIG. 13 is brought into the proximity of area of interest 90. Referring to FIG. 14B, there is shown a typical image from OCT data 92 in one embodiment.

Probe Embodiment

Figure 15:
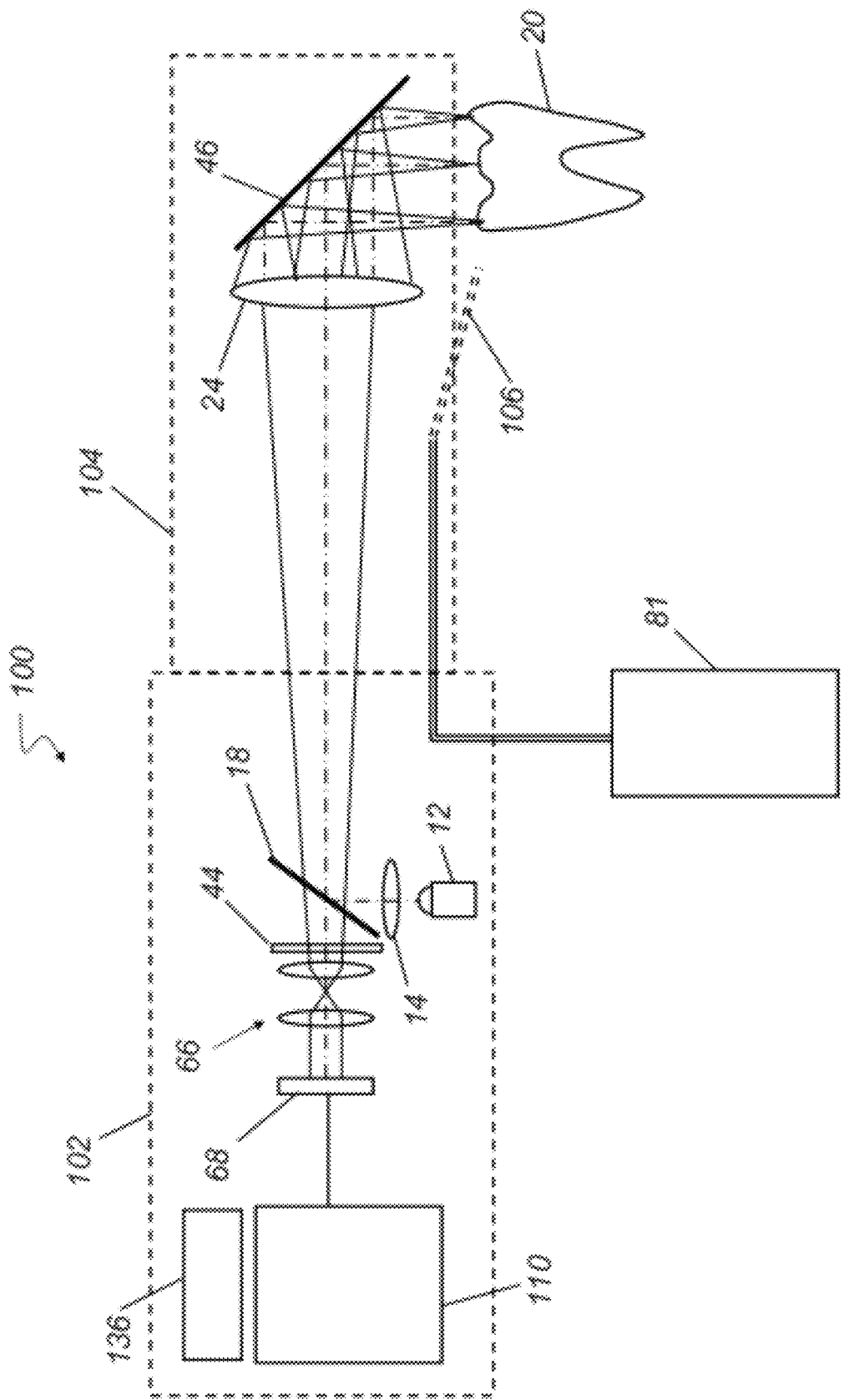
FIG. 15 is a block diagram showing an arrangement of a hand-held imaging apparatus in one embodiment.
Figure 18:
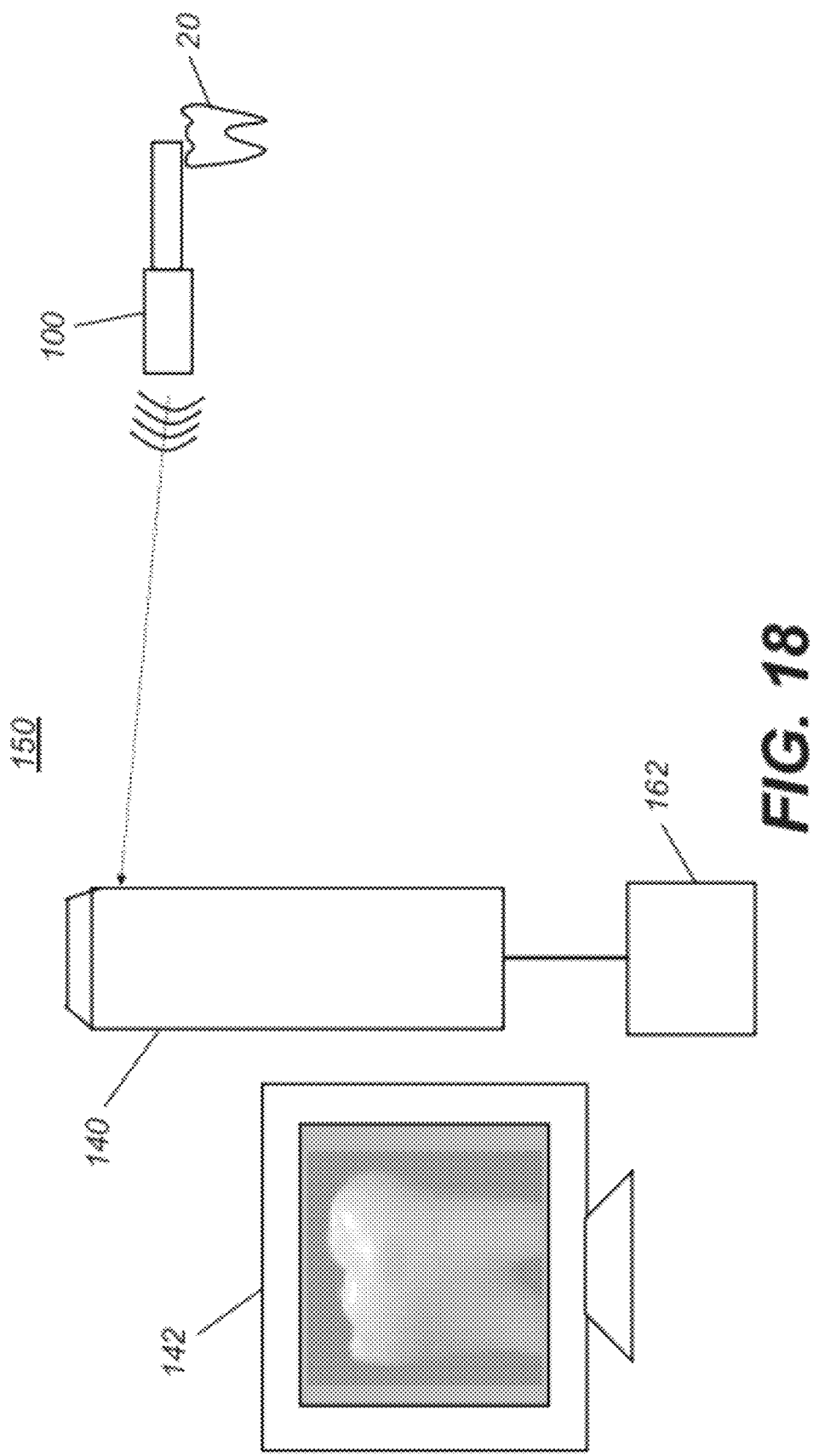
FIG. 18 is a block diagram showing a wireless dental imaging system in one embodiment.

The components of imaging apparatus 10 of the present invention can be packaged in a number of ways, including compact arrangements that are designed for ease of handling by the examining dentist or technician. Referring to FIG. 15, there is shown an embodiment of a hand-held dental imaging apparatus 100 according to the present invention. Here, a handle 102, shown in phantom outline, houses light source 12, sensor 68, and their supporting illumination and imaging path components. A probe 104 attaches to a handle 102 and may act merely as a cover or, in other embodiments, support lens 22 and turning mirror 46 in proper positioning for tooth imaging. Control circuitry 110 can include switches, memory, and control logic for controlling device operation. In one embodiment, control circuitry 110 can simply include one or more switches for controlling components, such as an on/off switch for light source 12. Control circuitry 110 can be a microprocessor in the probe or externally connected, configured with programmed logic for controlling probe functions and obtaining image data. Optionally, the function of control circuitry 110 can be performed at processing apparatus 38 (FIGS. 1-3). In other embodiments, control circuitry 110 can include sensing, storage, and more complex control logic components for managing the operation of hand-held imaging apparatus 100. Control circuitry 110 can connect to a wireless interface 136 for connection with a communicating device, such as computer workstation or server, for example. FIG. 18 shows an imaging system 150 using wireless transmission. Hand-held imaging apparatus 100 obtains an image upon operator instruction, such as with the press of a control button, for example. The image can then be sent to a control logic processor 140, such as a computer workstation, server, or dedicated microprocessor based system, for example. A display 142 can then be used to display the image obtained. Wireless connection of hand-held imaging apparatus 100 can be advantageous, allowing imaging data to be obtained at processing apparatus 38 without the need for hardwired connection. Any of a number of wireless interface protocols could be used, such as Bluetooth data transmission, as one example.

Dental imaging apparatus 100 may be configured differently for different patients, such as having an adult size and a children's size, for example. In one embodiment, removable probe 104 is provided in different sizes for this purpose. Alternately, probe 104 could be differently configured for the type of tooth or angle used, for example. Probe 104 could be disposable or could be provided with sterilizable contact components. Probe 104 could also be adapted for different types of imaging. In one embodiment, changing probe 104 allows use of different optical components, so that a wider angle imaging probe can be used for some types of imaging and a smaller area imaging probe used for single tooth caries detection. One or more external lenses could be added or attached to probe 104 for specific imaging types.

Probe 104 could also serve as a device for drying tooth 20 to improve imaging. In particular, fluorescence imaging benefits from having a dry tooth surface. In one embodiment, as shown in FIG. 15, a tube 106 providing an outlet for directing pressurized air or other drying gas from a pressurized gas source 81 onto tooth 20 is provided as part of probe 104. Probe 104 could serve as an air tunnel or conduit for pressurized air; optionally, separate tubing could be required for this purpose.

Figure 16:
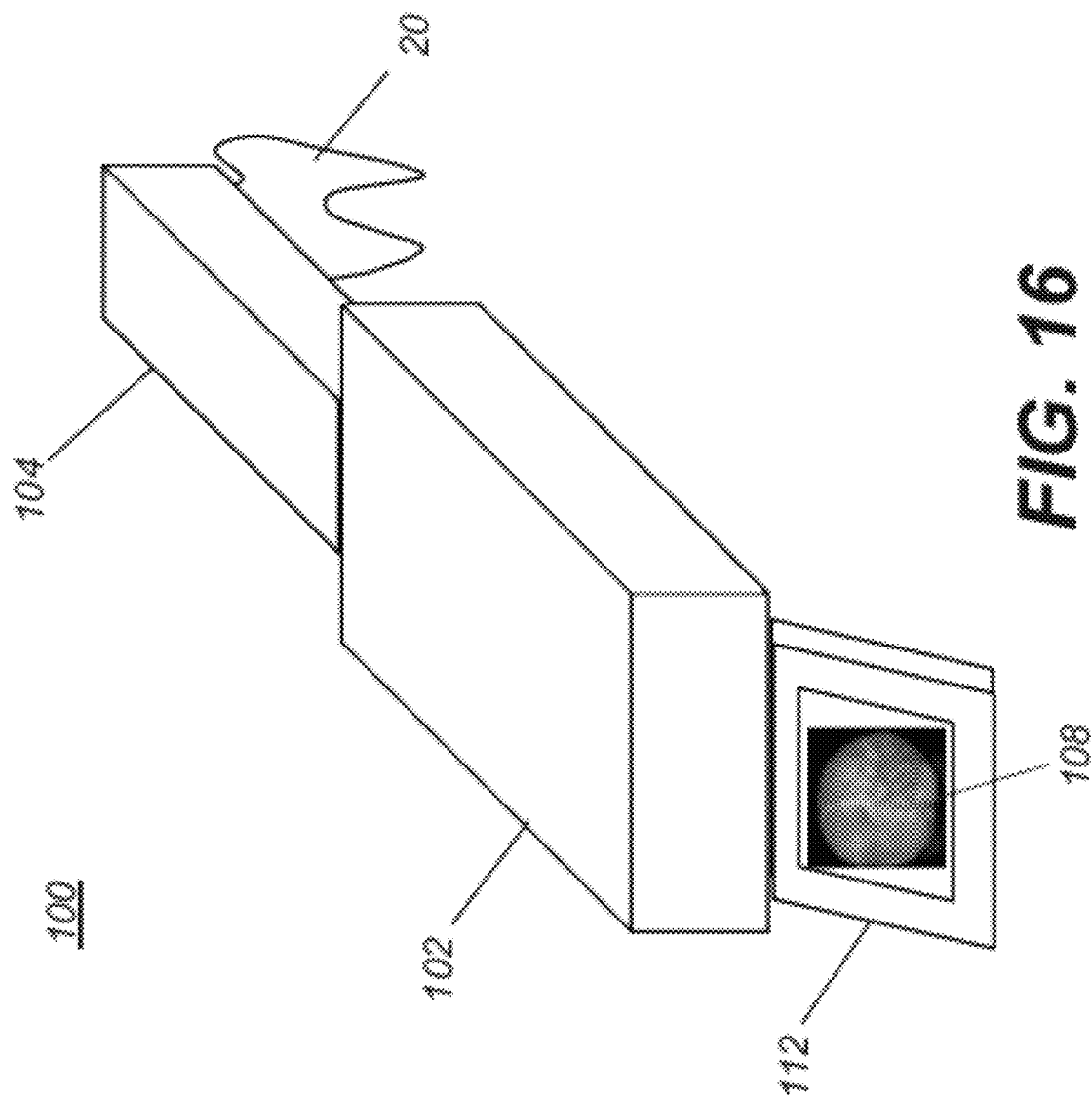
FIG. 16 is a perspective view showing an imaging apparatus having an integral display.

FIG. 16 shows an embodiment of hand-held imaging apparatus 100 having a display 112. Display 112 could be, for example, a liquid crystal (LC) or organic light emitting diode (OLED) display that is coupled to handle 102 as shown. A displayed image 108 could be provided for assisting the dentist or technician in positioning probe 104 appropriately against tooth 20. Using this arrangement, a white light source is used to provide the image on display 112 and remains on unless FIRE imaging is taking place. At an operator command entry, such as pressing a switch on hand-held imaging apparatus 100 or pressing a keyboard key, the white light image is taken. Then the white light goes off and the fluorescence imaging light source, for example, a blue LED, is activated. Once the fluorescence and white light images are obtained, the white light goes back on. When using display 112 or a conventional video monitor, the white light image helps as a navigation aid. Using a display monitor, the use of white light imaging allows the display of an individual area to the patient.

In order to obtain an image, probe 104 can be held in position against the tooth, using the tooth surface as a positional reference for imaging. This provides a stable imaging arrangement and fixed optical working distance. This configuration yields improved image quality and consistency. Placing probe 104 directly against the tooth has particular advantages for OCT imaging, as described earlier, since this technique operates over a small distance along the axis.

Figure 22:
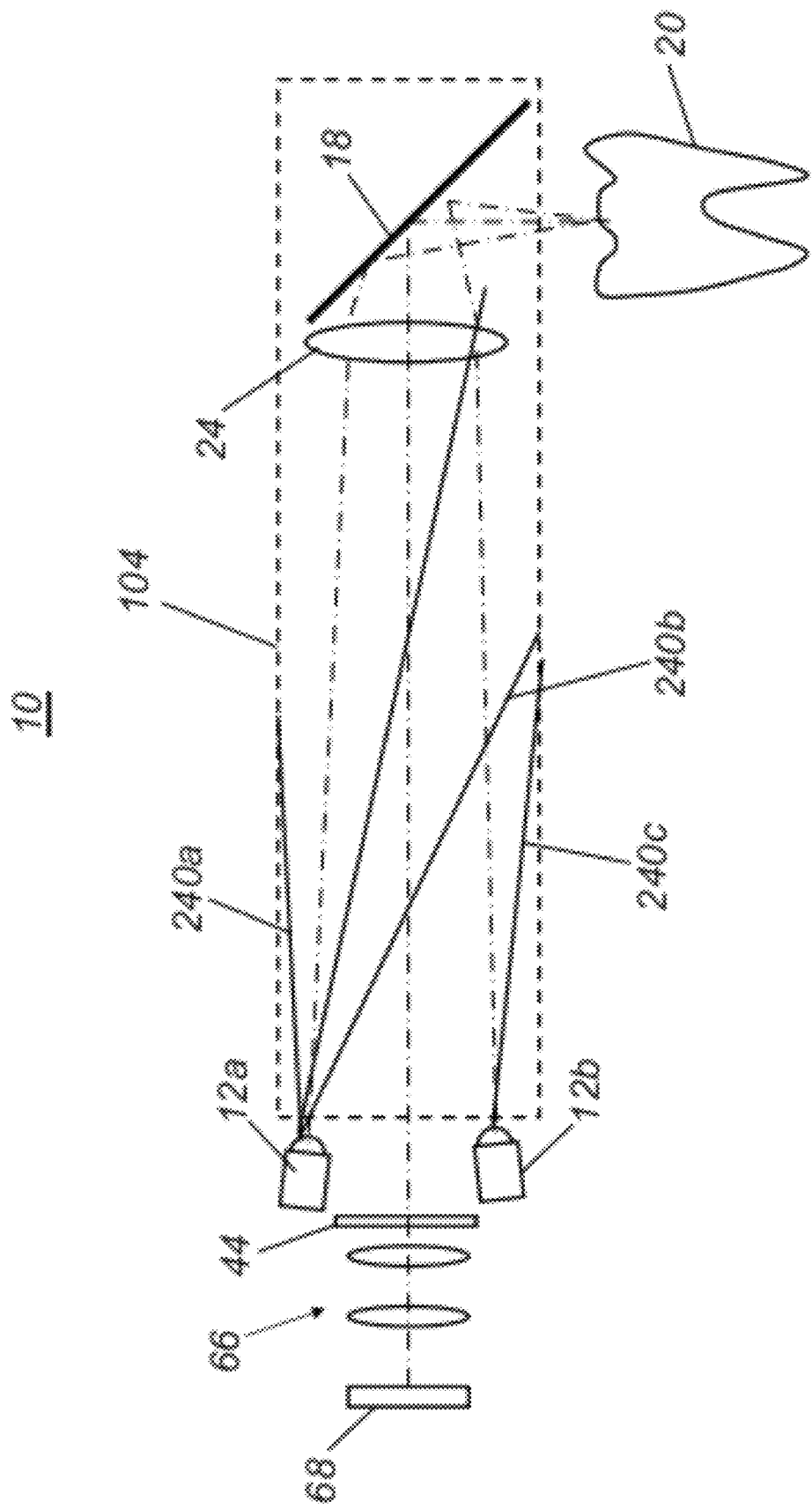
FIG. 22 is a block diagram showing the path of emitted light within the apparatus of the present invention.

In order to image different surfaces of the tooth, a folding mirror inside the probe, such as folding mirror 18 as shown in FIG. 22, is typically required. One problem related to this folding mirror is the undesired fogging of the mirror surface that often can occur. A number of methods are used in intraoral cameras to address this fogging problem. For example, in one embodiment, the mirror is heated so that its temperature approximates the temperature of the mouth. One drawback with this approach is that it requires an added heating element and current source for the heating element. In another embodiment of the present invention, an anti-fog coating is applied as a treatment to the mirror surface. With this arrangement, no additional components are required. Another embodiment is to bond an anti-fog film to the mirror surface.

The embodiments shown in FIGS. 11 and 12A-12C use LEDs as light sources 12a, 12b to illuminate tooth 20 directly, without any light-shaping optical element. Since the divergent angle of the light from LED is usually large, a sizable portion of the emitted light strikes the inner surface of the probe, as shown in FIG. 22. The large angle rays 240a, 240b and 240c in FIG. 22 hit the inner surface of the probe. If the probe inner surface is designed to be absorptive, the light hitting the surface is absorbed and does not reach tooth 20. In one embodiment, the inner surface of the probe is reflective, so that the light incident on this surface is reflected and eventually reaches the tooth. There are two advantages with this design. One advantage is increased efficiency, since all of the light reaches tooth 20 except for some absorption loss. Another advantage relates to the uniformity of the illumination on tooth 20. With a reflective inner surface, the probe operates as a light pipe. This integrates the light spatially and angularly, and provides uniform illumination to the tooth.

Imaging Software

One method for reducing false-positive readings or, similarly, false-negative readings, is to correlate images obtained from multiple sources. For example, images separately obtained using x-ray equipment can be combined with images that have been obtained using imaging apparatus 10 of the present invention. Imaging software, provided in processing apparatus 38 (FIGS. 1-3) allows correlation of images of tooth 20 from different sources, whether obtained solely using imaging apparatus 10 or obtained from some combination of devices including imaging apparatus 10.

Figure 17:
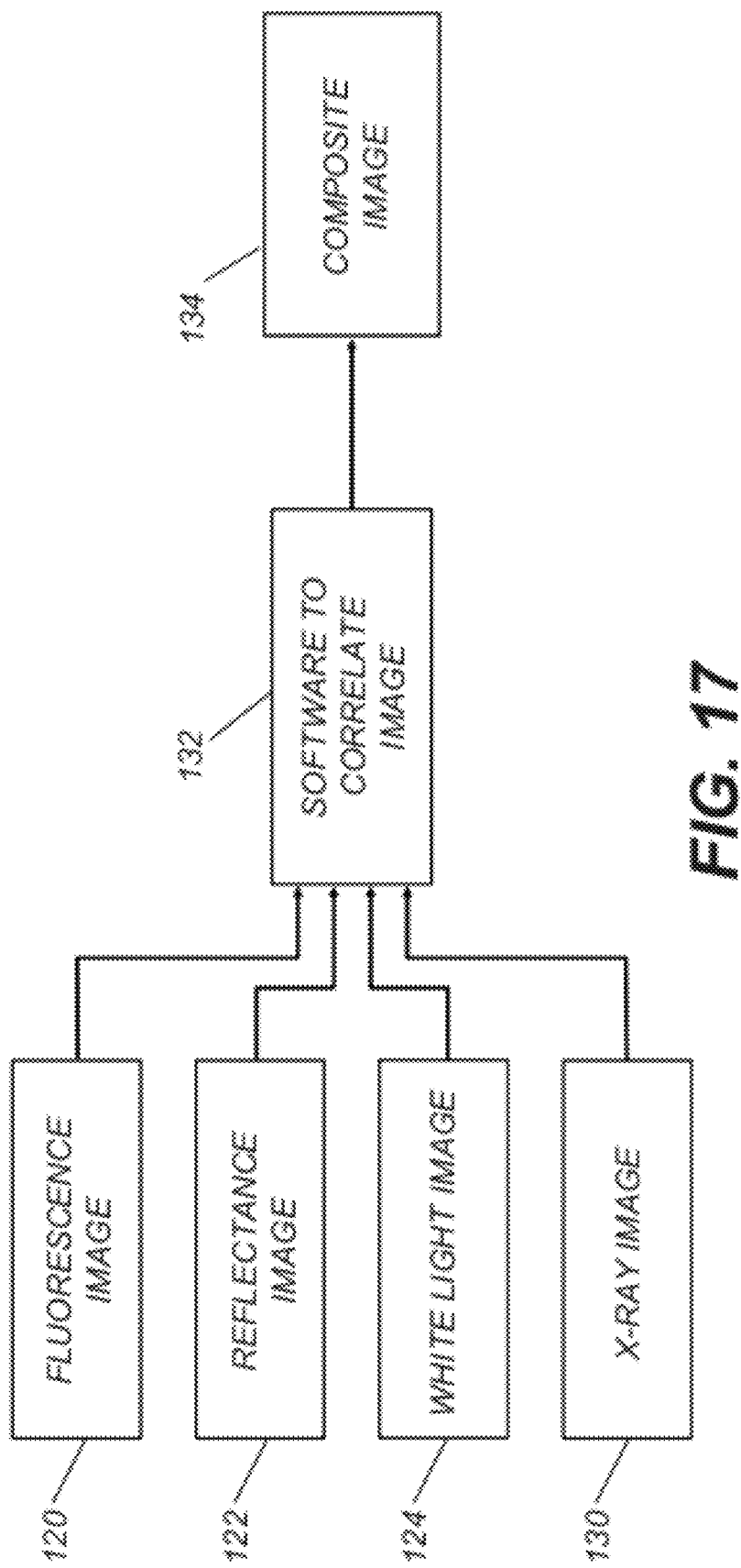
FIG. 17 is a block diagram showing combination of multiple types of images in order to form a composite image.

Referring to FIG. 17, there is shown, in block diagram form, a processing scheme using images from multiple sources. A fluorescence image 120, a reflectance image 122, and a white light image 124 are obtained from imaging apparatus 10, as described earlier. An x-ray image 130 is obtained from a separate x-ray apparatus. Image correlation software 132 takes two or more of these images and correlates the data accordingly to form a composite image 134 from these multiple image types. Composite image 134 can then be displayed or used by automated diagnosis software in order to identify regions of interest for a specific tooth. In one embodiment, the images are provided upon operator request. The operator specifies a tooth by number and, optionally, indicates the types of image needed or the sources of images to combine. Software in processing apparatus 38 then generates and displays the resultant image.

As one example of the value of using combined images, white light image 124 is particularly useful for identifying stained areas, amalgams, and other tooth conditions and treatments that might otherwise appear to indicate a caries condition. However, as was described earlier, the use of white light illumination is often not sufficient for accurate diagnosis of caries, particularly in its earlier stages. Combining the white light image with some combination that includes one or more of fluorescence and x-ray images helps to provide useful information on tooth condition. Similarly, any two or more of the four types of images shown in FIG. 17 could be combined by image correlation software 132 for providing a more accurate diagnostic image.

Imaging software can also be used to help minimize or eliminate the effects of specular reflection. Even where polarized light components can provide some measure of isolation from specular reflection, it can be advantageous to eliminate any remaining specular effects using image processing. Data filtering can be used to correct for unwanted specular reflection in the data. Information from other types of imaging can also be used, as is shown in FIG. 17. Another method for compensating for specular reflection is to obtain successive images of the same tooth at different light intensity levels, since the relative amount of specular light detected would increase at a rate different from light due to other effects.

Figure 20:
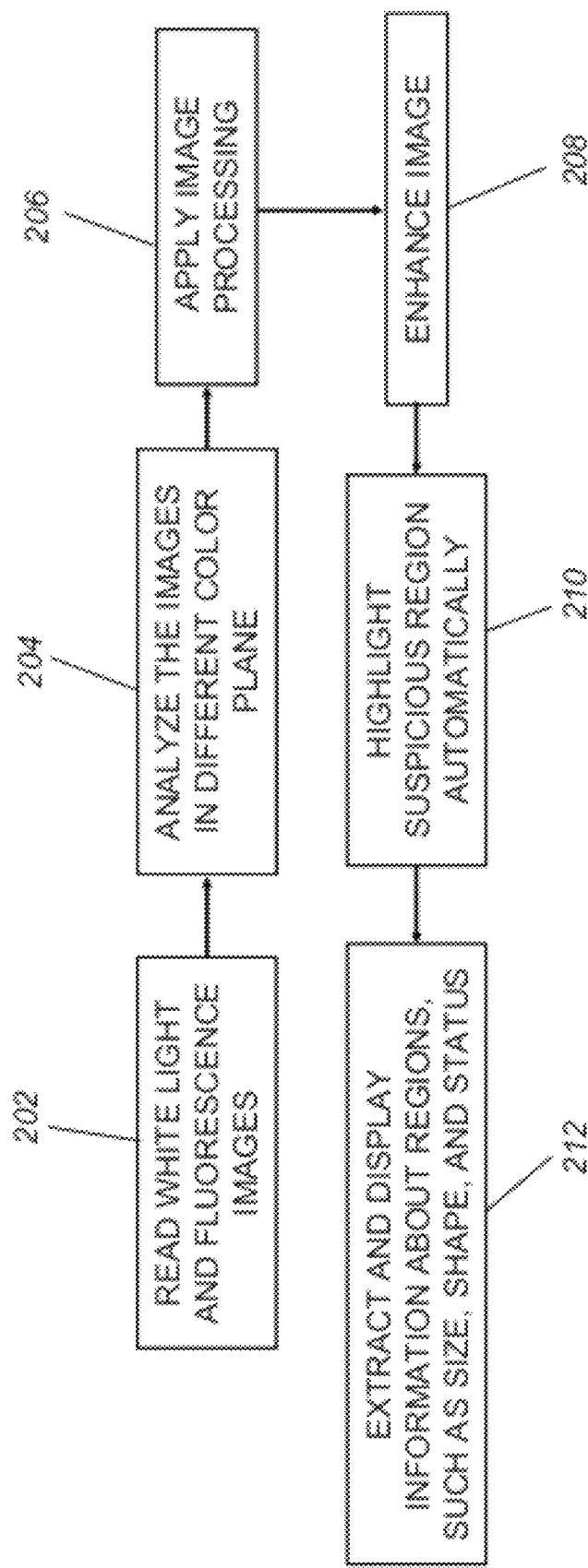
FIG. 20 is a logic flow diagram for image processing workflow.

Another key feature of the image processing software is to enhance the image obtained and automatically highlight suspicious areas such as white spots. FIG. 20 shows the flowchart for image processing workflow. As the first step 202, the software reads white light and fluorescence images. The software then analyzes the contents in different color planes in white light and fluorescence images in a step 204. With the information obtained from the white light and fluorescence images, different image processing algorithms such as color rendering, contrast enhancement, and segmentation, can be applied to enhance the image in steps 206 and 208. Some of the algorithms are discussed earlier with relation to image processing. Also, image processing algorithms can be used to identify the nature of each region, based on the color information in each color plane, and to highlight each region automatically in an enhancement step 210. As a final step 212, the tooth information, such as the size, shape and status of the suspicious area, can be extracted and displayed to the dental professionals.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention.

Figure 8:
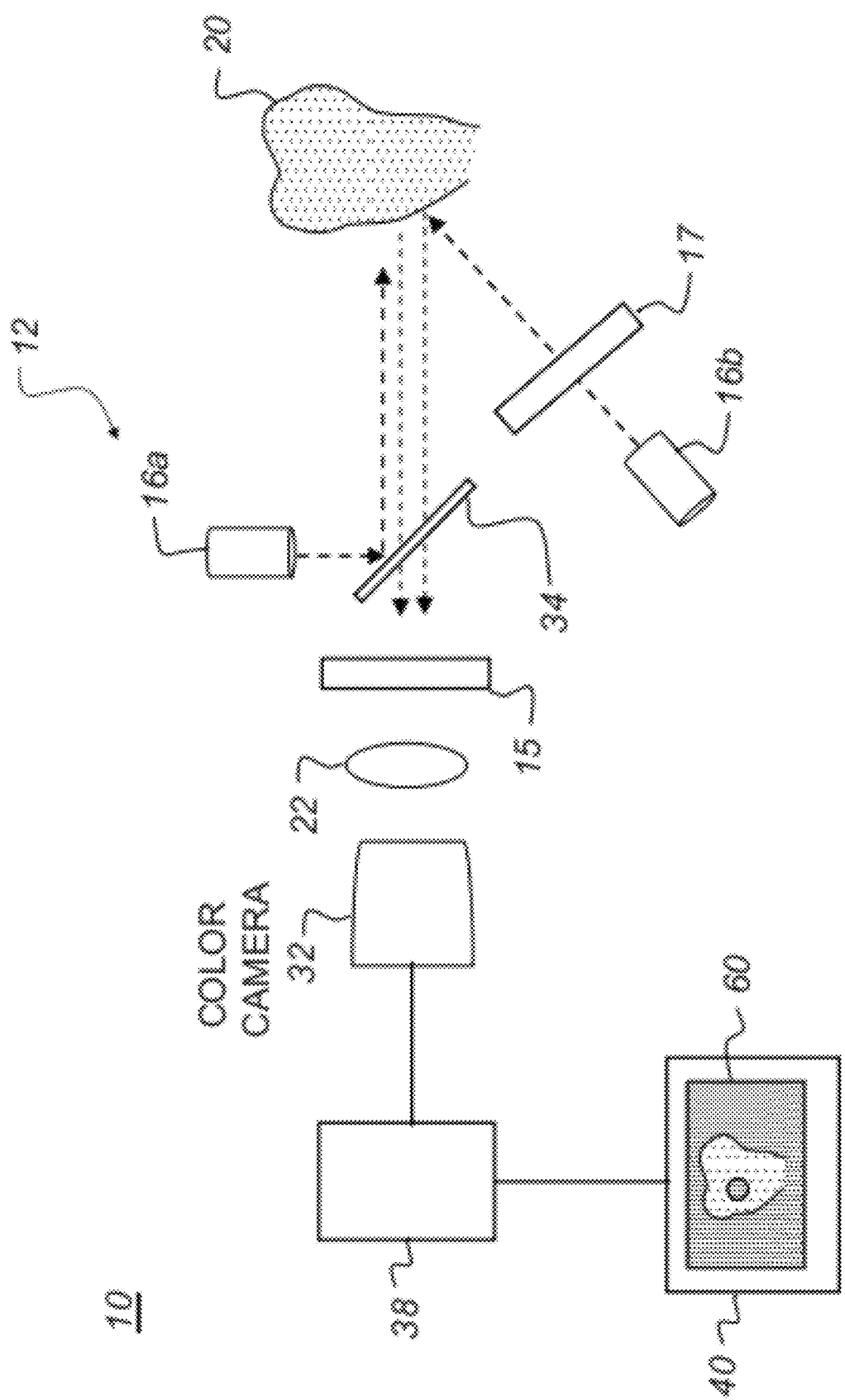
FIG. 8 is a schematic block diagram of an imaging apparatus for caries detection according to an alternate embodiment using multiple light sources.

For example, various types of light sources 12 could be used, with various different embodiments employing a camera or other type of image sensor. While a single light source 12 could be used for fluorescence excitation, it may be beneficial to apply light from multiple incident light sources 12 for obtaining multiple images. Referring to the alternate embodiment of FIG. 8, light source 12 might be a more complex assembly that includes one light source 16a for providing light of appropriate energy level and wavelength for exciting fluorescent emission and another light source 16b for providing illumination at different times. The additional light source 16b could provide light at wavelength and energy levels best suited for back-scattered reflectance imaging. Or, it could provide white light illumination, or other multicolor illumination, for capturing a white light image or multicolor image which, when displayed side-by-side with a FIRE image, can help to identify features that might otherwise confound caries detection, such as stains or hypo calcification. The white light image itself might also provide the back-scattered reflectance data that is used with the fluorescence data for generating the FIRE image. Supporting optics for both illumination and image-bearing light paths could have any number of forms. A variety of support components could be fitted about the tooth and used by the dentist or dental technician who obtains the images. Such components might be used, for example, to appropriately position the light source or sensing elements or to ease patient discomfort during imaging.

Thus, what is provided is an apparatus and method for caries detection at early and at later stages using combined effects of back-scattered reflectance and fluorescence.

PARTS LIST 10 imaging apparatus
12 light source
12a light source
12b light source
13 diffuser
14 lens
15 filter
16a light source
16b light source
17 filter
18 polarizing beamsplitter
20 tooth
22 lens
24 field lens
26 filter
28 filter
30 camera
32 camera
34 beamsplitter
38 processing apparatus
40 display
42 polarizer
42a polarizer
42b polarizer
44 analyzer
46 turning mirror
48 dichroic mirror
49a fiber bundle
49b fiber bundle
49c fiber bundle
49d fiber bundle
50 fluorescence image
52 reflectance image
54 white-light image
56 filter
58 carious region
60 FIRE image
62 threshold image
64 enhanced threshold FIRE image
66 lens
68 sensor 68a sensor
68b sensor
70 OCT imager
72 scanning element
74 lens
76 sample arm
78 dichroic mirror
80 OCT system
81 gas source
82 mirror
83 switch
84 scanning lens
90 area of interest
92 OCT data
96 filter curve
98 white light curve
100 imaging apparatus
102 handle
104 probe
106 tube
108 image
110 control circuitry
112 display
120 fluorescence image
122 reflectance image
124 white light image
130 x-ray image
132 image correlation software
134 composite image
136 wireless interface
140 control logic processor
142 display
150 imaging system
160 light source
162 beamsplitting and combining element
164 reference arm
166 detector and processing electronics
168 data acquisition hardware and computer system
202 step
204 step
206 step
208 step
210 step
212 step
220 object (tooth)
222 lens 1
224 intermediate image
226 lens 2
228 final image
240a ray
240b ray
240c ray
250a light source
250b light source
252a image
252b image
254 crosshair
256 cross point

The invention claimed is:

1. An apparatus for imaging a tooth comprising:
   (a) at least one light source providing incident light having a first spectral range for obtaining a reflectance image on the tooth and a second spectral range for exciting a fluorescence image of the tooth;
   (b) a polarizing beamsplitter in a path of the incident light, the polarizing beamsplitter directing light having a first polarization state toward the tooth and directing light from the tooth having a second polarization state along a return path toward a sensor, wherein the second polarization state is orthogonal to the first polarization state;
   (c) a lens positioned in the return path to direct image-bearing light from the tooth toward the sensor for obtaining image data from the portion of the light having the second polarization state; and
   (d) a long-pass filter in the return path, to attenuate light in the second spectral range and to transmit light in the first spectral range.

2. The apparatus of claim 1 wherein the polarizing beamsplitter is a wire grid polarizing beamsplitter.

3. The apparatus of claim 1 wherein said light source is comprised of a first light source having a first spectral range and a second light source having a second spectral range.

4. The apparatus of claim 3 wherein the light source further comprises a third light and a fourth light, wherein both the third and fourth lights direct a beam toward a point that corresponds with the focus of the lens.

5. The apparatus according to claim 4 further comprising control logic that automatically detects overlap of light from the third and fourth lights as focus and initiates capture of image data at the sensor.

6. The apparatus of claim 3 further comprising a band pass filter in the path of the second light source.

7. The apparatus of claim 1 wherein the lens is telecentric in object space.

8. The apparatus of claim 1 wherein the sensor is a complementary metal oxide semiconductor (CMOS) sensor.

9. The apparatus of claim 1 wherein the sensor is a charged couple device (CCD) sensor.

10. The apparatus of claim 1 wherein the light source is taken from the group consisting of an LED, an incandescent bulb, a super luminescent diode, a diode-pumped solid-state crystal source, and a diode-pumped rare earth-doped fiber source.

11. The apparatus of claim 1 further comprising an analyzer in the return path.

12. The apparatus of claim 1 wherein the first spectral range is between about 400 nm and 700 nm.

13. The apparatus of claim 1 further comprising:
   (e) a display coupled to the sensor for presenting the image data obtained therefrom.

14. The apparatus of claim 1 further comprising:
   (e) an interferometer coupled along the optical path for obtaining an image of a portion of the tooth using optical coherence tomography.

15. The apparatus of claim 1 wherein the second spectral range is between about 300 nm and 500 nm.

16. The apparatus according to claim 1 further comprising an outlet for directing a pressurized gas toward the tooth.

17. The apparatus according to claim 1 further comprising a switch enabling an operator to enable either the light in the second spectral range or the light in the first spectral range.

18. The apparatus according to claim 1 further comprising a second lens for imaging an intermediate image formed by the first lens onto the sensor.

19. An apparatus for imaging a tooth comprising:
   (a) a handle portion for handling and positioning by an operator;
   (b) a probe portion, separable from the handle portion, for placement in the proximity of the tooth;
   (c) an optical subsystem housed within the handle and probe portions comprising:
      (i) at least one light source providing incident light having a first spectral range for obtaining a reflectance image on the tooth and a second spectral range for exciting a fluorescence image of the tooth;

(ii) a polarizing beamsplitter in a path of the incident light, the polarizing beamsplitter directing light having a first polarization state toward the tooth and directing light from the tooth having a second polarization state along a return path toward a sensor, wherein the second polarization state is orthogonal to the first polarization state;

(iii) a lens positioned in the return path to direct image-bearing light from the tooth toward the sensor for obtaining image data from the portion of the light having the second polarization state; and (iv) a long-pass filter in the return path, to attenuate light in the second spectral range and to transmit light in the first spectral range.

20. The apparatus according to claim 19 wherein the handle portion further comprises an operator control for initiating operation to obtain an image.

21. The apparatus according to claim 19 further comprising a wireless interface for sending image data to a communicating device.

22. The apparatus according to claim 19 further comprising a display for operator viewing of the image data obtained.

23. The apparatus according to claim 22 wherein the display is taken from the group consisting of a liquid crystal (LC) display and an organic light emitting diode (OLED) display.

24. The apparatus according to claim 19 further comprising an outlet for directing a pressurized gas toward the tooth.

25. The apparatus according to claim 19 wherein the probe portion is disposable.

26. The apparatus according to claim 19 further comprising at least one folding mirror in the optical path.

27. The apparatus according to claim 26 wherein the at least one folding mirror is treated to reduce fogging effects.

28. The apparatus according to claim 26 wherein the probe is in communication with a display and wherein the at least one folding mirror cooperates with other components along the optical path to track the tooth surface during movement of the probe.

29. The apparatus according to claim 19 wherein the probe portion comprises a reflective inner surface.

* * * * *